United States Patent
Laurent-Applegate et al.

(10) Patent No.: US 9,278,122 B2
(45) Date of Patent: *Mar. 8, 2016

(54) FETAL SKIN CELL PROTEIN COMPOSITIONS FOR THE TREATMENT OF SKIN CONDITIONS, DISORDERS OR DISEASES AND METHODS OF MAKING AND USING THE SAME

(71) Applicant: Merz GmbH & Co. KGaA, Allschwil (CH)

(72) Inventors: Lee Laurent-Applegate, Bercher (CH); Patrick Hohlfeld, Lausanne (CH)

(73) Assignee: MERZ GMBH & CO. KGAA, Allschwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/893,048

(22) Filed: May 13, 2013

(65) Prior Publication Data

US 2013/0251651 A1    Sep. 26, 2013

Related U.S. Application Data

(63) Continuation of application No. 12/710,437, filed on Feb. 23, 2010, now Pat. No. 8,449,879, which is a continuation of application No. 11/226,558, filed on Sep. 14, 2005, now abandoned.

(60) Provisional application No. 60/610,613, filed on Sep. 15, 2004, provisional application No. 60/641,067, filed on Jan. 3, 2005.

(51) Int. Cl.
| | |
|---|---|
| *A01N 63/00* | (2006.01) |
| *A61K 38/17* | (2006.01) |
| *A61K 38/01* | (2006.01) |
| *A61K 8/64* | (2006.01) |
| *A61K 45/06* | (2006.01) |
| *A61Q 17/04* | (2006.01) |

(52) U.S. Cl.
CPC ............... *A61K 38/1709* (2013.01); *A61K 8/64* (2013.01); *A61K 38/014* (2013.01); *A61K 45/06* (2013.01); *A61Q 17/04* (2013.01)

(58) Field of Classification Search
CPC ......... A61K 38/14; A61K 8/64; A61K 45/06; A61K 38/1709; A61Q 17/04; A61Q 19/00; A61Q 19/08
See application file for complete search history.

(56) References Cited

U.S. PATENT DOCUMENTS

| | | | |
|---|---|---|---|
| 4,418,691 A | | 12/1983 | Yannas et al. |
| 4,458,678 A | | 7/1984 | Yannas et al. |
| 5,015,584 A | | 5/1991 | Brysk |
| 5,068,315 A | * | 11/1991 | Buultjens et al. ............ 530/324 |
| 5,460,939 A | | 10/1995 | Hansbrough et al. |
| 5,489,304 A | | 2/1996 | Orgill et al. |
| 5,512,475 A | | 4/1996 | Naughton et al. |
| 5,541,107 A | | 7/1996 | Naughton et al. |
| 5,798,334 A | | 8/1998 | Cutroneo |
| 5,866,167 A | * | 2/1999 | Van Bossuyt ................. 424/520 |
| 5,976,878 A | | 11/1999 | Boyce |
| 6,039,760 A | | 3/2000 | Eisenberg |
| 6,110,208 A | | 8/2000 | Soranzo et al. |
| 6,179,872 B1 | | 1/2001 | Bell et al. |
| 6,270,781 B1 | | 8/2001 | Gehlsen |
| 8,449,879 B2 | | 5/2013 | Laurent-Applegate et al. |
| 2002/0068051 A1 | * | 6/2002 | Dai et al. .................... 424/93.21 |
| 2003/0175256 A1 | | 9/2003 | Laurent-Applegate et al. |
| 2004/0170615 A1 | * | 9/2004 | Soo ............................ 424/93.21 |

FOREIGN PATENT DOCUMENTS

| | | |
|---|---|---|
| JP | 6316530 A | 11/1994 |
| WO | WO-9624661 A1 | 8/1996 |
| WO | WO-9836704 A1 | 8/1998 |
| WO | WO-9840027 A1 | 9/1998 |
| WO | WO-9943270 A1 | 9/1999 |
| WO | WO-9949878 A1 | 10/1999 |
| WO | WO-00076437 A1 | 12/2000 |
| WO | WO-0132129 A2 | 5/2001 |
| WO | WO-03068287 A1 | 8/2003 |
| WO | WO-2004053101 A2 | 6/2004 |
| WO | WO-2006/092668 A2 | 9/2006 |
| WO | WO-2006/092668 A3 | 9/2006 |

OTHER PUBLICATIONS

Dale B..A. et al. Expression of epidermal keratins and filaggrin during human fetal skin development, The Journal of Cell Biology, Oct. 1985, vol. 101, pp. 1257-1269.*
Wilson M.C et al. A and B forms of the androgen receptor are expressed in a variety of human tissues, Molecular and Cellular Endocrinology, 1996, vol. 120, pp. 51-57.*
Fauza D.O. et al. Videofetoscopically assisted fetal tissue engineering: Skin replacement, Journal of Pediatric Surgery, Feb. 1998, vol. 33, No. 2, pp. 357-361.*
Lorenz H.P. et al. The fetal fibroblast: the effector cell of scarless fetal skin repair, Plast. Reconstruct. Surg., 1995, vol. 96, pp. 1251-1261.*
"Average Animal Gestation Periods and Incubation Times." *MSN Encarta-Multimedia*. Web. Dec. 7, 2005.
"Prevent." Merriam-Webster OnLine. Web. Dec. 8, 2005.
"Various Treatments of Facial Wrinkles." Deborah Watson, M.D. Dec. 29, 2001. Web. Dec. 6, 2013. http://www.deborahwatsonmd.com/procedures/procedure-facial.html.
Bianchini et al. "Immunological Safety Evaluation of a Horse Collagen Haemostatic Pad." *Arneimittelforschung*. 51.5(2001):414-419.
Cass et al. "Scar Wars: Implications of Fetal Wound Healing for the Pediatric Burn Patient." *Pediat. Pediatr. Surg. Int.* 12.7(1997):484-489.

(Continued)

Primary Examiner — Satyendra K Singh
(74) *Attorney, Agent, or Firm* — Mintz Levin Cohn Ferris Glovsky and Popeo, P.C.; Terri Shieh-Newton; Linyu L. Mitra

(57) ABSTRACT

The present invention provides methods and compositions designed for treating a subject suffering from skin conditions, disorders or diseases. The compositions include fetal skin cell proteins obtained from fetal skin cells after induced cell lysis.

16 Claims, 9 Drawing Sheets

(56) References Cited

OTHER PUBLICATIONS

Chin et al. "Differential Expression of Receptor Tyrosine Kindases and Shc in Fetal and Adult Rat Fibroblasts: Towards Defining Scarless Versus Scarring Fibroblast Phenotypes." *Plast. Reconstr. Surg.* 105.3(2000):972-979.

Ennis et al. "Leg Ulcers: A Practical Approach to the Leg Ulcer Patients." *Ostomy Wound Manage.* 41(1995):52S-63S.

Erdag et al. "Cryopreservation of Fetal Skin is Improved by Extracellular Trehalose." *Cryobiol.* 44.3(2002):218-228.

French et al. "Chondrogenic Differentiation of Adult Dermal Fibroblasts." *Ann. Biomed. Eng.* 32.1(2004):50-56.

Hirai et al. "Epimorphin: A Mesenchymal Protein Essential for Epithelial Morphogenesis." *Cell.* 69.3(1992):471-481.

Hohlfeld et al. "Tissue Engineered Fetal Skin Constructs for Paediatric Burns." *Lancet.* 366.9488(2005):840-842.

Kolokol'tsova et al. "Prospects of Certified Human Fetal Fibroblasts in the Treatment of Wounds of Various Etiology." *Vestnik Rossiiskoi Akademii Meditsinskikh Nauk.* 3(1998):32-35. (English Abstract Only).

Lorenz et al. "Scarless Wound Repair: A Human Fetal Skin Model." *Dev.* 114(1992):253-259.

Maas-Szabowski et al. "Keratinocyte Growth Regulation in Defined Organotypic Cultures Through IL-1-Induced Keratinocyte Growth Factor Expression in Resting Fibroblasts." *J. Invest. Dermatol.* 114.6(2000):1075-1084.

Maessen-Visch. "Atrophie Blanche." *Eur. J. Obst. Gynecol. Reprod. Biol.* 90(2000):1-2.

Metts. "Vulvodynia and Vulvar Vestibulitis: Challenges in Diagnosis and Management." *Am. Fam. Physician.* 59.6(1999):1-12.

Moulin et al. "Fetal and Adult Human Skin Fibroblasts Display Intrinsic Differences in Contractile Capacity." *J. Cell. Physiol.* 188(2001):211-222.

Nemecek et al. "Safety Evaluation of Human Living Skin Equivalents." *Toxic. Path.* 27.1(1999):101-103.

Pandya et al. "Disorders of Hyperpigmentation." *Dermatologic Clinics.* 18.1(2000):91-98.

Parenteau et al. "The Organotypic Culture of Human Skin Keratinocytes and Fibroblasts to Achieve Form and Function." *Cytother.* 9.1-3(1992):163-171.

Rager et al. "Cutaneous Melanoma: Update on Prevention, Screening, Diagnosis, and Treatment." *Am. Fam. Physician.* 76.11(2007):1614, 1618.

Southwood et al. "Instrument Sterilization, Skin Preparation, and Wound Management." *Vet. Clin. N. America. Equine Pract.* 12.2(1996):173-194.

\* cited by examiner

BEFORE          AFTER
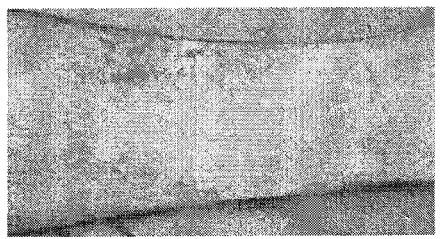 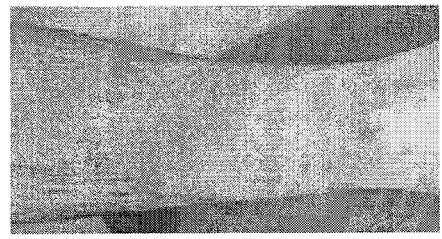
Figure 5
Figure 5

BEFORE AFTER

BEFORE　　　　　　　　　AFTER

BEFORE  AFTER

BEFORE AFTER

FETAL SKIN CELL PROTEIN COMPOSITIONS FOR THE TREATMENT OF SKIN CONDITIONS, DISORDERS OR DISEASES AND METHODS OF MAKING AND USING THE SAME

RELATED APPLICATIONS

This application is a continuation of U.S. Ser. No. 12/710,437, filed Feb. 23, 2010, which is a continuation of U.S. Ser. No. 11/226,558, filed Sep. 14, 2005, which claims priority to, and the benefit of, U.S. Provisional Patent Application No. 60/610,613, filed Sep. 15, 2004 and U.S. Provisional Patent Application No. 60/641,067, filed Jan. 3, 2005. The contents of these applications are incorporated by reference in their entireties.

FIELD OF THE INVENTION

The present invention relates to methods and compositions designed for treating a subject suffering from skin conditions, disorders or diseases. The compositions contain fetal skin cell proteins obtained from fetal skin cells after induced cell lysis.

BACKGROUND OF THE INVENTION

Up to a certain age of gestation, fetal skin heals with no or only very minor scar formation (also called scarless repair or scarless healing) after wounding (Dang C et al., Clin Plast Surg 2003: 30, 13-23), which indicates an optimal (balanced) orchestration (regulation) of a coordinated cellular response in fetal skin during a specific time period of gestation. Newborn, young and adult skin (corresponding to non fetal skin), however, heal with scar formation after wounding, which indicates that the coordinated cellular response in non-fetal skin is less optimal or less balanced than in fetal skin.

In large animals and humans, scarless repair after wounding occurs up to mid-gestation to the early third trimester. At around this time period, fetal wound healing transitions from scarless to healing with scar formation upon wounding of fetal skin. In skin, scarless repair in the fetus is characterized by regeneration of an organized dermis with normal appendages (hair follicle, sweat gland, apocrine gland). Scarless healing is believed to be, at least partially, the result of a relative lack of inflammation, what corresponds to a balanced (optimal) pro- and anti-inflammatory response after wounding.

The ability to heal scarlessly appears to be intrinsic to fetal skin and is probably the result of the orchestrated interaction of many regulatory proteins including cytokines. This is illustrated infra.

Scarless fetal wounds heal with little inflammation, and the onset of scarring during fetal repair correlates with the presence of an acute inflammatory infiltrate (G. P. Yang et al. Wound Rep Reg 2003; 11: 411-418). In addition, introduction of inflammation into normally scarless-healing wounds results in increases in collagen deposition and scarring. This suggests an important function of inflammation during scar formation. As the immune system develops and its resultant inflammatory response increases, scar formation occurs at the repair site. Synthesis and remodeling of the extracellular matrix (ECM) by wound fibroblasts is likely the major determinant of dermal architecture after repair. Differences between scarring and scarless collagen architecture may be partly explained by phenotypic differences between adult and fetal fibroblasts.

Fetal and adult fibroblasts display differences in synthetic rates of collagen, hyaluronic acid (HA), and other ECM components. In vitro, fetal fibroblasts synthesize more type III and IV collagen than their adult counterparts. Fetal fibroblasts can simultaneously proliferate (or grow) and synthesize collagen. Fetal fibroblasts have a greater ability to migrate into collagen gels than do adult fibroblasts. Increasing cell density diminishes HA production in the adult but has no effect on fetal fibroblast HA synthesis.

The transforming growth factor (TGF) isoforms TGF-beta 1 and TGF-beta 2 (both isoforms are growth factors; growth factors belong to the cytokine protein family) have profibrotic functions (induce fibrosis) and promote scar formation. Their expression is increased in normal wound healing, and exogenous administration of this growth factor to adult wounds increases collagen, proteoglycan, and inflammatory cell accumulation. TGF-beta 1 also decreases matrix metalloproteinases and increases endogenous inhibitors of matrix metalloproteinase expression, which may favor collagen accumulation and scarring. Moreover, treatment of adult rat wounds with neutralizing antibody to TGF-beta 1 and TGF-beta 2 reduces scar formation. Treatment with fibromodulin, a TGF-beta modulator, has also been reported to reduce postnatal scarring.

In addition, it appears that the relative proportion of TGF-beta isoforms and not the absolute amount of any one isoform determines the wound repair outcome. In scarless fetal wounds, TGF-beta 3 (isoform of TGF-beta) expression is increased while TGF-beta 1 expression is unchanged. Conversely, TGF-beta 1 expression is increased and TGF-beta 3 decreased in scarring fetal wounds. Treatment of adult rat wounds with exogenous TGF-beta 3 reduces scar formation. These data suggest that the ratio of TGF-beta 3 to TGF-beta 1 may determine whether skin architecture is restored or scar forms after wounding.

Interleukins (belong to the cytokine protein family) regulate the chemotaxis and activation of inflammatory cells. Interleukin-6 (IL-6) stimulates monocyte chemotaxis and macrophage activation while interleukin-8 (IL-8) attracts neutrophils and stimulates neovascularization. Wounding stimulates a rapid increase in IL-6 and IL-8, which persists in the adult but disappears quickly in the fetus. Platelet-derived growth factor (PDGF, growth factor belonging to the cytokine protein family) induces adult fibroblast production of IL-6. In turn, the addition of IL-6 to fetal wounds produces early scarring. In fetal, compared to adult, fibroblasts IL-6 and IL-8 expression are lower at baseline and after stimulation with PDGF. Interleukin-10 (IL-10) has an anti-inflammatory function by decreasing production of IL-6 and IL-8. For instance, it has been shown in adult mouse that wounds treated with an IL-10 overexpressing adenoviral vector exhibited reduced inflammation and scarless healing.

PDGF and the fibroblast growth factor (FGF) family are additional profibrotic cytokines. PDGF, a potent mitogen and chemoattractant for fibroblasts, has prolonged expression during scar formation but disappears quickly in fetal wounds. For instance, it was shown that treatment of fetal rabbit wounds with PDGF induces a marked increase in acute inflammation, fibroblast recruitment, and collagen deposition. The FGF family of cytokines, including keratinocyte growth factor-1 and -2 (growth factors belonging to the cytokine protein family), has greater expression with increasing gestational age in fetal skin and during adult wounding.

In contrast, a mitogen for endothelial cells, vascular endothelial growth factor (VEGF, growth factor belonging to the cytokine protein family), increases twofold in scarless wounds while its expression remains unchanged in scarring fetal wounds. Thus, an increased stimulus for angiogenesis and vascular permeability may assist the rapid healing of fetal wounds.

The precise mechanisms of scarless healing remain unknown, despite the great increase in knowledge gained over the past decade. Scarless fetal wound repair is a tightly regulated (orchestrated) process involving various cellular mediators such as cytokines and other proteins.

Current therapies do not provide a mechanism for scarless healing. Therefore, it is an object of the present invention to provide compositions and methods to use the disclosed compositions to treat subjects suffering from a skin condition, disorder or disease and in need of scarless healing and/or in need of a balanced response to skin inflammation.

SUMMARY OF THE INVENTION

The present invention provides a composition for treating a subject suffering from a skin condition, disorder or disease which includes one or more fetal skin cell proteins and an acceptable carrier, where the fetal skin cell proteins are obtained from one or more fetal skin cells after cell lysis.

The fetal skin cells are obtained at 6-24 weeks of gestation or more preferably at 12-16 weeks of gestation. The fetal skin cells are obtained from whole fetal skin tissue or fetal skin tissue fragments. The fetal skin cells can include fibroblasts, keratinocytes, melanocytes, Langerhans cells, Merkel cells or combinations and mixtures thereof. Preferably, the fetal skin cells comprise fetal fibroblasts. The fetal skin cells can be immortalized. The fetal skin cells can be obtained from a cell bank or a cell line.

The fetal skin cell proteins can be purified or can include one or more cellular components. The fetal skin cells proteins can include cytokines, enzymes, hormones, extracellular matrix structural proteins, neuropeptides or neuropeptide antagonists. The cytokines can include growth factors, interleukins, lymphokines, monokines, interferons, colony stimulating factors or chemokines or combinations and mixtures thereof. The fetal skin cell proteins can be incorporated in the composition at a concentration of between 0.001% to 95%. More preferably, incorporated in the composition at a concentration of between 0.01% to 5%. Most preferably, incorporated in said composition at a concentration of between 0.05% to 0.25%.

The composition can further include analgesics, anesthetics, anti-inflammatory agents, antihistamine agents, antioxidants, counter irritants, antimicrobial agents, antibacterial agents, antifungal agents, preservatives, protein stabilizing agents, protease inhibitors, skin protectant agents, sunscreens or combinations and mixtures thereof.

The composition is suitable for topical, mucosal, ocular, rectal or vaginal administration. Preferably, the composition is suitable for topical administration.

The composition can be an ointment, lotion, cream, foam, mousse, spray, aerosol, emulsion, nanoemulsion, microemulsion, mask, gel, hydrogel, solution, sponge or dispersion suitable for pharmaceutical or cosmetic applications. The composition can be a water-in-oil or oil-in-water emulsion or a water-in-oil or oil-in-water emulsion based cream.

The cell lysis is induced and is not spontaneous. The cell lysis can be performed mechanically, physically or chemically. Preferably, the cell lysis is performed by one or more cycles of freeze-thawing. The cell lysis can be performed with between 100 to 60,000,000 of fetal skin cells suspended in one milliliter of an aqueous system. More preferably, the cell lysis is performed with between 10,000,000 to 20,000,000 of fetal skin cells. The aqueous system can be a physiological buffer system. More preferably, the aqueous system is a phosphate buffered saline system. The aqueous system can further include one or more protein stabilizing chemicals, protease inhibitors, anti-microbial agents, anti-bacterial agents, anti-oxidants, preservatives or combinations and mixtures thereof.

The present invention also provides methods of treating a skin or mucosal condition, disorder or disease comprising administering a composition to a subject in need thereof wherein the composition includes one or more fetal skin cell proteins and an acceptable carrier, thereby treating said condition, disorder or disease. The skin or mucosal condition, disorder or disease can be an inflammatory skin or mucosal condition, neurogenic or neuroinflammatory skin or mucosal condition, acute or chronic wounds, acute or chronic ulcers or burns.

The present invention also provides methods of treating an inflammatory skin condition comprising administering a composition to a subject in need thereof wherein the composition includes one or more fetal skin cell proteins and an acceptable carrier, thereby treating said condition. The inflammatory skin condition can be vulvar vestibulitis syndrome, dysesthetic vulvodynia, vulvodynia, psoriasis, dermatitis, atopic dermatitis, eczema, contact dermatitis, allergic contact dermatitis, dermatitis herpetiformis, generalized exfoliative dermatitis, vulvar lichen sclerosus, sebaceous cysts, seborrheic dermatitis, rosacea, acne, keloids, pruritus, atrophie blanche, dandruff, diaper rash, photo-dermatoses, peri-ulcers, scars or xerosis.

The present invention also provides methods of treating vulvodynia comprising administering a composition to a subject in need thereof wherein the composition includes one or more fetal skin cell proteins and an acceptable carrier, thereby treating said condition. Preferably, the vulvodynia can be vulvar vestibulitis syndrome or vulvar lichen sclerosus. The method can further include administering corticosteroids, estrogen, progesterone, lidocaine, capsaicin, isotretinoin, interferon-$\alpha$, interferon-$\beta$, interferon-$\gamma$, dapsone, acyclovir, tricyclic anti-depressants or possible combinations or mixtures thereof.

The present invention also provides methods of treating one or more wounds, ulcers or burns comprising administering a composition to a subject in need thereof wherein composition includes one or more fetal skin cell proteins and an acceptable carrier, thereby treating said one or more wounds or burns. The method can further include administering films, hydrocolloids, hydrogels, foams, petrolatum, silicon, silicon sheets, calcium alginates or cellophane. The method composition can be administered with external compression. Preferably, the external compression is administered by one or more bandages. The bandages can be lightweight conforming-stretch bandages, light support bandages or compression bandages.

The present invention also provides methods of improving the appearance of skin in combination with cosmetic or dermatological treatments comprising administering a composition to a subject in need thereof wherein the composition includes one or more fetal skin cell proteins and an acceptable carrier, thereby treating said skin. The cosmetic and/or dermatological treatment can be a chemical peel, physical peel, dermabrasion, microdermabrasion, light and/or laser treatment, intense pulse light treatment, radiofrequency treatment, thermal treatment, oxygen and/or ozone treatment, electrosurgical resurfacing or coblation, superfluous hair removal, tattoo removal, botulinum toxin injections, injection with fillers, syringe liposculpturing, syringe fat transfer, cosmetic or non-cosmetic surgical procedure, cryosurgery or cryotherapy and/or a topical medication containing alpha-hydroxy acids, azelaic acid, benzoic acid, benzoylperoxide, beta-hydroxy acids, betamethasone, citric acid, clindamycin, corticosteroids, diclofeneac, dithranol, fluorouracil, glycolic acids, hydrocortisone, hydrocortisone acetate, hydroquinone, indomethacin, isotretinoin, kojic acid, lactic acid, metronidazole, phenol, retinoic acid, retinol, retinaldehyde, retinoyl beta-glucuronide, salicylic acid, selenium sulfide, sodium sulfacetamide, sulfur, tazarotene, tretinoin, trichloroacetic acid, urea or derivatives thereof or any combinations of these cosmetic or dermatological treatments. The cosmetic or dermatological treatment can be a rosacea treatment.

Preferably, the subject in need thereof treated by the methods provided by the present invention is an animal. Preferably, the animal is a horse. More preferably, the subject is a human.

BRIEF DESCRIPTION OF THE DRAWINGS

FIG. 5 is a photograph showing the efficacy of Cream 1 containing 0.05% fetal skin cell proteins in treating psoriasis. A representative example of a psoriasis patient is shown before and after cream use for several weeks.

DETAILED DESCRIPTION OF THE INVENTION

Figure 1:
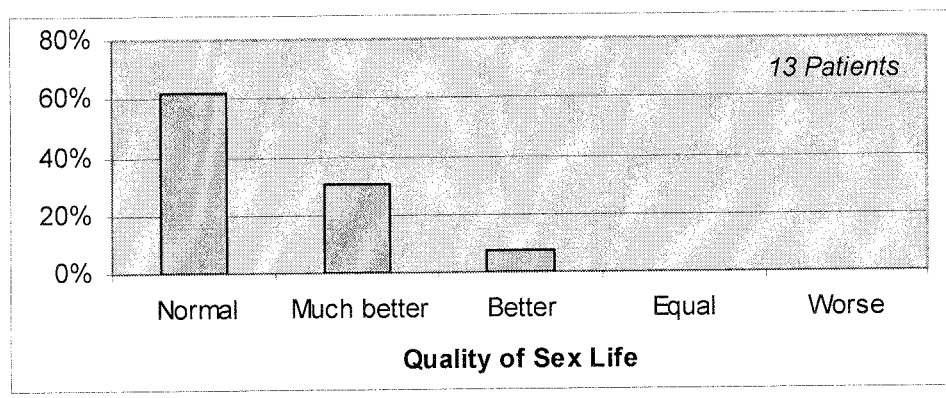
FIG. 1 is a graph showing the efficacy of Cream 1 containing 0.05% fetal skin cell proteins in treating vulvar vestibulitis syndrome as assessed by a quality of sex life interview.

Various studies indicate that numerous skin conditions, disorders and/or diseases have often multi-factorial causes, often with activation of complex immunologic and inflammatory pathways. For instance, a broad network of cytokines orchestrating the development of disease-related mechanisms exists in inflammatory, neurogenic and/or neuroinflammatory skin conditions, disorders and/or diseases. The regulation of coordinated cellular responses during skin regeneration, skin repair or wound healing further requires the interaction of many cytokines (Physiol Rev 83: 2003, 835-870).

It may therefore be speculated that numerous inflammatory, neurogenic and/or neuroinflammatory skin conditions, disorders or diseases can be more successfully treated by combination of specific actives and/or by combination of specific treatment regimens.

Today, most inflammatory, neurogenic and/or neuroinflammatory skin conditions, disorders and/or diseases are treated with a single active agent. Rarely, two, or up to three active agents are combined in the same drug product to obtain enhanced, synergistic or complementary drug activity and efficacy. As an example, the combination of two external analgesic drugs such as hydrocortisone and pramoxine hydrochloride in the same formulation is given. In another example, a combination therapy for psoriasis using topical corticosteroids (betamethasone dipropionate and diflucortolone, respectively) together with salicylic acid resulted in improved efficacy (Am J Clin Dermatol 5, 2004, 71-77). With respect to topical applications, other similar examples are known for those skilled in the art. These examples represent drug products combining two or more synthetic chemicals as active drug entities in the same composition. Similar biopharmaceutical compositions combining two or more active proteins are less frequent. For instance, no such commercial available biopharmaceutical product is currently marketed.

Induced cell lysis (induced cell disruption) of fetal skin cells, which are obtained at the age of gestation where fetal skin heals with no or little scar-formation after wounding, provides fetal skin cell proteins for a balanced (optimal) orchestration (regulation) of skin inflammation, skin regeneration and skin repair. Induced is defined as planned, intended, designed and/or predetermined by humans and/or mankind. Induced is further defined as the opposite of spontaneous or naturally occurring in nature. By mankind induced cell lysis is further defined as not apoptosis (programmed cell death) and not necrosis (unprogrammed cell death) due to changes in the culture conditions of cells.

Induced cell lysis can be achieved by mechanical, physical and/or chemical methods. For instance, one and more cycles of freeze-thawing are an example of an induced cell lysis.

Induced cell lysis allows obtaining proteins in one single step at a specific and defined moment of the cell status (e.g.: passage number, viability, cell cycle, level of confluence, etc.). As a result, induced cell lysis allows obtaining a mixture of proteins of a specific protein composition (corresponds to a naturally balanced, optimal protein mixture) present at the moment of cell lysis. This composition is different than when incorporating viable cells into a composition, where the proteins are released (expelled by cells by exocytosis) and/or otherwise produced by the cell over time and/or during and after apoptosis or necrosis. Additionally, induced cell lysis allows obtaining: (1) proteins not normally released by the cell, (2) proteins without being modified during the release process or exocytosis, (2) proteins at differing degree of post-translational modifications (Post-translational modifications may involve the formation of disulfide bridges and/or the attachment of any of a number of biochemical functional groups, such as acetate, phosphate, various lipids and carbohydrates. Enzymes may also remove one or more amino acids from the amino end of the polypeptide chain, or cut the polypeptide within the chain.), and/or (3) proteins in the pro-form (e.g. inactive precursor of active protein). Proteins in the pro-form are often more stable than the final (active) protein. Proteins in the pro-form can be activated by enzymes (e.g. hydrolases) in the composition and/or once they reach the target tissue and/or the target cell (e.g. skin, skin cells). Furthermore, induced cell lysis allows obtaining proteins in their natural, cell-like environment, but free of a cell wall, what helps to additionally stabilize (prevent degradation, hydrolysis, conformational changes and/or denaturation) the proteins. Another advantage of inducing cell lysis is the fact that the so obtained proteins do not contain, or contain to a lesser amount, proteins commonly released/produced by stressed cells. This may occur in a composition containing cells. Generally, cells in cellular compositions become stressed due to lack of cell nutrients, pH-changes, temperature changes, oxidative stress and/or other environmental, physical and chemical factors influencing the growth and/or the viability of the cells during the administration of the composition. Some proteins produced by such stressed cells are of pro-inflammatory nature, are of no or only little clinical efficacy, and/or may be otherwise harmful.

The US Patent Application 2003/0175256, incorporated herein by reference, is hereby given as a representative example for cellular compositions. The compositions include undifferentiated fetal skin cells that are either integrated with a collagen matrix or a carrier.

In one of the preferred embodiments, the cell lysis is induced by freeze/thaw or freeze-thawing. The technique involves freezing (e.g. in liquid nitrogen, in a dry ice and alcohol bath, etc.) fetal skin cells and/or a fetal skin cell suspension and then thawing the material at room temperature and/or 37° C. This method of induced cell lysis causes cells to swell and ultimately break as ice crystals form during the freezing process and then contract during thawing. Generally, multiple cycles of freeze-thawing are necessary for efficient lysis. Freeze/thaw has been shown to effectively release proteins located in the cell.

The said proteins obtained after said induced cell lysis comprise a mixture of one or more proteins and may or may not contain other skin cell constituents such as lipids, polysaccharides, nucleic acids and/or other bio-molecules. A bio-molecule is a chemical that naturally occurs in living organisms and cells. Bio-molecules consist primarily of carbon (C) and hydrogen (H), along with nitrogen (N), oxygen (O), phosphorus (P) and sulfur (S). Besides these elements (C, H, N, O, P and S), other elements sometimes are incorporated but these are less common. Lipids, polysaccharides and nucleic acids are examples of bio-molecules.

Proteins are polymers of amino acids linked via peptide bonds; the proteins may be composed of one, two or more polypeptide chains. The proteins can be of differing protein types (e.g. water soluble proteins, membrane bound proteins, cell surface proteins, structural proteins, homologue proteins, etc) and/or of differing enzyme classes (oxidoreductases, transferases, hydrolases, lyases, isomerases and/or ligases) and can be glycosylated to differing degrees. The proteins may be also called peptides and/or polypeptides.

Said induced cell lysis allows obtaining said proteins as a physiological, natural or optimal (or naturally balanced) mixture of proteins present in the cell at the moment of induced cell lysis. In contrast to obtaining said proteins by above defined induced cell lysis, the incorporation of viable cells into a composition for the treatment of skin conditions, disorders or diseases does not allow obtaining said proteins. The proteins obtained when viable cells are incorporated into a composition are of different characteristics (e.g. protein structure, protein composition, presence of cytokines, stability, etc) and/or activity (e.g. stimulation of proliferation, anti-inflammatory properties, etc.) than the proteins obtained by induced cell lysis.

Viable cells are cells which are of measurable cell viability. Cell viability can be measured using a variety of cell viability assays including but not limited to measurement of metabolic activity (e.g.: MTT [3-(4,5-dimethylthiazol-2-yl)-2,5-diphenyltetrazolium bromide] assay, ATP [adenosine tri-phosphate] assay), survival and growth in tissue culture (e.g. proliferation assay), functional assay, metabolite incorporation (e.g. fluorescence-based assays), structural alteration, and membrane integrity (e.g. LDH (lactate dehydrogenase) assay). Each viability assay method is based on different definitions of cell viability.

In addition, the said fetal skin cell proteins obtained after said induced cell lysis can be manipulated, separated, purified, concentrated, modified, fractionated, stabilized and stored. Furthermore, the said fetal skin cell proteins can be integrated into differing carriers (delivery forms, release forms, formulations, devices) with or without modifications. In one of the preferred embodiments of this innovation, the said carrier is a suitable topical preparation for pharmaceutical applications and/or cosmetic applications. A suitable topical preparation contains suitable (for l'Homme de l'Art) ingredients for cosmetic and/or pharmaceutical applications and is prepared using suitable (for l'Homme de l'Art) methods of preparation. The said topical preparation is applied to the body surfaces such as skin, scalp and/or mucous membranes. Mucous membranes are linings of ectodermic origin, covered in epithelium, and are involved in absorption and secretion. They line various body cavities that are exposed to the external environment and internal organs. It is at several places continuous with skin: at the nostrils, the lips, the ears, the genital area including penis, vulva and vagina, and the anus.

Compositions designed for treating a subject suffering from a skin condition, disorder or disease comprise one or more fetal skin cell proteins obtained from one or more fetal skin cells by induced cell lysis. The said fetal skin cells are of human and/or animal origin. They are obtained from one or more fetal skin tissue samples and/or fetal skin tissue fragments at any age of gestation when skin tissue is present during the development of the fetus. In one of the preferred embodiment of this invention, fetal skin tissue, fetal skin tissue samples and/or fetal skin tissue fragments to produce said fetal skin cells is obtained at an age of gestation when fetal skin shows wound healing with no or minimal scar formation after surgery in utero.

The invention describes the use of said fetal skin tissue up to mid-gestation to the early third trimester in order to obtain said fetal skin cell proteins. In one of the preferred embodiment, said fetal skin tissue is taken (surgically removed, taken by biopsy or otherwise sampled) between 6-24 weeks of gestational age. In another preferred embodiment, the fetal skin tissue is taken between 8-18 weeks of gestational age. In the preferred embodiment, said fetal skin tissue is taken between 12-16 weeks of age of gestation from a human fetus.

The said fetal skin cells are obtained as a part or as the whole skin tissue by skin tissue sampling, taking a skin biopsy, or skin tissue collection. Fetal skin cells can be obtained by outgrowing from fetal skin tissue, tissue fragments and/or tissue samples placed in culture plates under appropriate culture conditions using standard cell culture techniques. Fetal skin cell cultures or fetal skin cell lines can be obtained, from which cell banks and/or cell lines can be established. Fetal skin cells can be cultured and expanded (grown, multiplied) up to high passage numbers and/or high cell doubling numbers. The fetal skin cells are preferentially cultured and expanded up to a passage number and/or doubling number where the cell characteristics, in particular the gene and/or protein expression profile of the cells, are similar or comparable to the cell characteristics of the cells obtained from the fetal skin tissue. Often, the fetal skin cells are cultured and expanded up to a low passage and/or cell doubling number.

The fetal skin cells can be at any differentiation or proliferation state. They can be either undifferentiated or differentiated. The fetal skin cells comprise all skin cell types present in the fetal epidermis and the fetal dermis including but not limited to fibroblasts, keratinocytes, melanocytes, Langerhans cells and Merkel cells. The invention includes both the use of a single skin cell type as well as the use of any combinations or mixtures of fetal skin cell types at any ratios of cell numbers. In one of the preferred embodiments, one or more fetal skin fibroblasts are used. In another preferred embodiment, one or more fetal skin keratinocytes are used. In a further embodiment, the combination of one or more fetal fibroblasts together with one or more fetal keratinocytes is used.

Fetal fibroblasts are defined as cells originating or taken from fetal skin, which can be cultured and be grown (proliferate) under cell culture conditions (e.g. media) identically or similarly than commonly used for adult dermal fibroblasts by the skilled artisan. Fetal keratinocytes are defined as cells originating or taken from fetal skin, which can be cultured and be grown (proliferate) under cell culture conditions (e.g. media) identically or similarly than commonly used for adult epidermal keratinocytes by the skilled artisan. Fetal melanocytes are defined as cells originating or taken from fetal skin, which can be cultured and be grown (proliferate) under cell culture conditions (e.g. media) identically or similarly than commonly used for adult melanocytes by the skilled artisan. Fetal Langerhans cells are defined as cells originating or taken from fetal skin, which can be cultured and be grown (proliferate) under cell culture conditions (e.g. media) identically or similarly than commonly used for adult Langerhans cells by the skilled artisan. Fetal Merkel cells are defined as cells originating or taken from fetal skin, which can be cultured and be grown (proliferate) under cell culture conditions (e.g. media) identically or similarly than commonly used for adult Merkel cells by the skilled artisan.

Optionally, the fetal skin cells or fetal skin cell lines can be mitotically inactivated before use. Mitotic inactivation can be performed by gamma-irradiation, mitotic inhibitors and/or through incubation with mitomycin.

Optionally, the fetal skin cells can be immortalized and/or transfected with a gene. Continuous or immortalized fetal skin cells can be derived from fetal skin tissue. Continuous or immortalized fetal skin cells include, but are not limited to immortalized fetal skin fibroblasts, and/or immortalized fetal skin keratinocytes, and/or immortalized fetal melanocytes. They are derived from said fetal skin tissue of human and/or animal origin. Said continuous or immortalized fetal skin cells are designed to maintain the differentiation potential of primary (not immortalized or not continuous) fetal skin cells and/or express differentiation proteins characteristic of primary fetal skin fibroblasts, primary fetal skin keratinocytes and/or fetal melanocytes, even after high (numerous) passages. More specifically, it is an object of the invention to obtain continuous fetal skin cells (or continuous fetal skin cell lines), which maintain the ability to produce (express, synthesize) proteins involved in anti-inflammatory related processes and/or proteins involved in the orchestration (regulation) of skin regeneration, skin repair and/or wound healing, even after high (numerous) passages.

The one or more fetal skin cell proteins are obtained from one or more fetal skin cells by said induced cell lysis (cell disruption). The fetal skin cell proteins can be either composed of predominantly proteins (>75% of dry weight) or can include other biomolecules and/or cell derived organic and/or inorganic components including but not limited to amino acids, extracellular matrix components (e.g. hyaluronic acid), DNA, RNA, fatty acids, fatty acid esters, lipids, sugars, monosaccharides, polysaccharides, minerals, water, salts as well as any other extra- or intracellular material. The fetal skin cell proteins can be used with or without further processing and/or manipulation. For example, the fetal skin cell proteins can be used after one or several purification and/or separation steps. For instance, fetal skin cell proteins containing no, little or less RNA and/or DNA can be obtained by removing or partially removing RNA and/or DNA by appropriate manipulation, separation, and/or purification steps. Likewise, one or more manipulation, purification and/or separation steps may be included after induced cell lysis in order to obtain a single and specific protein at high concentration or purity. Similarly, one or more manipulation, purification and/or separation steps may be included after induced cell lysis in order to obtain a defined protein mixture comprising two or more proteins at high concentration or purity.

In other group of embodiments of this innovation, the fetal skin cell proteins comprise only the supernatant (liquid, containing soluble compounds that is left behind after a mixture is centrifuged) obtained after centrifugation of said fetal skin cell proteins. In further embodiments of this innovation, the fetal skin cell proteins comprise only the cell pellet (cellular material left at the bottom of the centrifugation tube) obtained after centrifugation of the fetal skin cell proteins.

In one of the preferred embodiments of this invention, the fetal skin cell proteins comprise a naturally balanced mixture of fetal skin cell proteins, which are obtained after induced cell lysis of fetal skin cells cultured under standard (normal or common) cell culture conditions for adult dermal fibroblasts (e.g. using Dulbecco's Modification of Eagle's Medium (DMEM) supplemented with about 10% fetal bovine serum (FBS, also called fetal calf serum or FCS) in a 37° C., 5% to 10% $CO_2$ and >80% humidity incubator). Alternatively, the use of serum-free (no FCS or FBS) culture media (or medium) and/or serum-depleted culture media (e.g. <10% fetal bovine serum) is also regarded as standard cell culture conditions for adult dermal fibroblasts. The supplementation (addition) of the culture media with antibiotics (e.g. penicillin, streptomycin, etc.) is also regarded as standard cell culture conditions.

In other group of embodiments, the fetal skin cell proteins comprise a mixture of fetal skin cell proteins, which are obtained after induced cell lysis of fetal skin cells cultured under non-standard (abnormal) culture conditions. A non-standard cell culture conditions include, but are not limited to cell culture under oxidative and/or chemical stress, physical and/or mechanical stress and/or elevated or lowered culture temperatures over a limited or extended period of time. The supplementation of the culture media with selected chemicals and/or proteins (e.g. PDGF, etc.) to increase the production of specific cytokines by fetal skin cells is also regarded as non-standard cell culture conditions.

In one of the preferred embodiments of this innovation, the said fetal skin cell proteins comprise cytokines. Cytokine refers to a generic name for a diverse group of proteins and peptides which act as regulators and which, either under normal or pathological conditions, modulate the functional activities of individual cells and tissues. These proteins also mediate interactions between cells directly and regulate processes taking place in the extracellular environment.

As set forth in the "The Cytokine Handbook" (4. ed., 2003, Academic Press, by Angus W. Thomson and Michael T. Lotze) and/or in the "Cytokines Online Pathfinder Encyclopedia" (http://www.copewithcytokines.de/cope.cgi) which are specifically incorporated herein by reference, cytokines comprise growth factors, interleukins, lymphokines, monokines, interferons, colony stimulating factors, chemokines, and a variety of other proteins.

Most but not all cytokines are glycoproteins. Many genes encoding cytokines can give rise to a variety of variant forms of cytokines by means of alternative splicing, yielding molecules with slightly different but biologically significant bioactivities. In many cases the expression patterns of different forms of cytokines or of members of a cytokine family are overlapping only partially, suggesting a specific role for each factor. Membrane-bound forms have been described also for many cytokines, and some may be associated also with the extra-cellular matrix.

Almost all cytokines are pleiotropic effectors showing multiple biological activities. In addition, multiple cytokines often have overlapping activities and a single cell frequently interacts with multiple cytokines with seemingly identical responses (cross-talk). One of the consequences of this functional overlap is the observation that one factor may frequently functionally replace another factor altogether or at least partially compensate for the lack of another factor. Since most cytokines have ubiquitous biological activities, their physiologic significance as normal regulators of physiology is often difficult to assess.

Many cytokines show stimulating or inhibitory activities and may synergise (act in synergy) or antagonize (act as antagonist) the actions of other cytokines and/or other factors. A single cytokine may elicit reactions also under certain circumstances which are the reverse of those shown under other circumstances.

The type, the duration, and also the extent of cellular activities induced by a particular cytokine can be influenced considerably by the micro-environment of a cell, depending, for example, on the growth state of the cells (sparse or confluent), the type of neighboring cells, cytokine concentrations, the combination of other cytokines present at the same time, and even on the temporal sequence of several cytokines acting on the same cell. Under such circumstances combinatorial effects thus allow a single cytokine to transmit diverse signals to different subsets of cells.

Cytokines are important mediators involved in embryogenesis and organ development and their activities in these processes may differ from those observed post-natally (after birth). In addition they play a key role in neuroimmunological, neuroendocrinological, and neuroregulatory processes. Cytokines are important positive or negative regulators of mitosis, differentiation, migration, cell survival and cell death, and transformation.

The biological activities of cytokines are mediated by specific membrane receptors which can be expressed on virtually all cell types known. Their expression is also subject to several regulatory mechanisms although some receptors are expressed also constitutively. Cytokine receptor proteins have been shown to share a number of characteristics. Many receptors are members of cytokine receptor families Many receptors are multi-subunit structures that bind ligands and at the same time possess functions as signal transducers due to their intrinsic tyrosine kinase activity. Many receptors often share common signal transducing receptor components in the same family, which explains, at least in part, the functional redundancy of cytokines.

It is the cross-communication between different signaling systems that eventually allows the integration of a great diversity of stimuli, which a cell can be subjected to under varying physiological situations.

Although some recombinant cytokines are now in clinical use, and attempts are made to develop hybrid molecules from known cytokines which possess the advantages of the respective factors, but not their disadvantages, one must be aware of the fact that current knowledge is still limited. Cytokines are powerful two-edged "weapons" that can trigger a cascade of reactions, and may show activities that often go beyond the single highly specific property which it is hoped they possess. New factors are being discovered constantly and they extend our knowledge about the cytokine network.

Among the cytokine group are the interleukins as well as growth and colony-stimulating factors. Interleukin is the generic name for a group of well-characterized cytokines that are produced by leukocytes and other cell types including skin cells. They have a broad spectrum of functional activities that regulate the activities and capabilities of a wide variety of cell types, and they are particularly important as members of the cytokine network that regulate inflammatory and immune responses. Growth factors are proteins that bind to receptors on the cell surface, with the primary result of activating cellular proliferation and/or differentiation. Many growth factors are quite versatile, stimulating cellular division in numerous different cell types; while others are specific to a particular cell-type.

In addition, the said fetal skin cell proteins may comprise enzymes from all known enzyme classes including but not limited to oxidoreductases (EC 1), transferases (EC 2), hydrolases (EC 3), lyases (EC 4), isomerases (EC 5) and ligases (EC 6) as published in *Enzyme Nomenclature* 1992 (Academic Press, San Diego, Calif.) and its supplements.

The said oxidoreductases may include but are not limited to oxidoreductase acting on a peroxide as acceptor (sub-class EC 1.11; including peroxidases (EC 1.11.1) such as catalase and/or glutathione peroxidase), and/or oxidoreductases acting on superoxide radicals as acceptor (sub-class EC 1.15; including superoxide dismutase (SOD) and/or superoxide reductase).

The said fetal skin cell proteins may also comprise peptides and/or proteins including but not limited to hormones, neuropeptides, neurohormones and/or their respective receptor antagonists.

In another embodiment of this invention, the fetal skin cell proteins comprise proteins contained in the conditioned culture media of one or more said fetal skin cells. The conditioned culture media is the solution containing the spent (used, depleted) culture media and proteins and other cell derived components released into the culture media during the cell culture period by the cells.

The said fetal skin cell proteins can be integrated (incorporated, included, mixed, blended, emulsified, homogenized and/or added) into a variety of compositions. A composition is formed by integrating the one or more fetal skin cell proteins into a carrier, formulation or device suitable for topical, mucosal, ocular, rectal and/or vaginal application to obtain compositions designed for treating a subject suffering from skin conditions, disorders or diseases. In one of the preferred embodiments, the fetal skin cell proteins are incorporated into a topical preparation suitable for pharmaceutical and/or cosmetic applications.

In another embodiment of this invention, conditioned culture media obtained after culturing said fetal skin cells is integrated into a carrier, formulation or device suitable for topical, mucosal, ocular, rectal and/or vaginal application.

Skin conditions, disorders or diseases treated by the said compositions include, but are not limited to inflammatory skin conditions, neurogenic or neuroinflammatory skin conditions, acute and chronic wounds, acute and chronic ulcers, and burns.

In one of the preferred embodiments, the inflammatory, neurogenic and/or neuroinflammatory skin conditions is vulvodynia comprising vulvar vestibulitis and vulvar lichen sclerosus.

In another embodiment of this invention, said skin conditions disorders or diseases treated by the said compositions include mucosal conditions, disorders or diseases where mucosa or mucosal tissue is adjacent to the treated skin.

Examples of skin conditions, disorders, or diseases treated by the compositions of the invention further include acne, atopic dermatitis, allergic contact dermatitis, atrophie blanche, dandruff, dermatitis, hand eczema, herpetiformis, diaper rash, eczema, generalized exfoliative dermatitis, keloids, localized and/or generalized pruritus, photo-dermatoses, peri-ulcers, psoriasis, scars, sebaceous cyst, seborrheic dermatitis, rosacea, and/or xerosis.

Examples of skin conditions, disorders or diseases treated by the compositions of the invention also include wounds; including acute and chronic wounds, ulcers; including acute and chronic ulcers, and/or burns.

Examples of skin conditions, disorders, or diseases treated by the compositions of the invention further include wounds, ulcers, and/or burns during and/or after single or repetitive treatment with a skin allograft, skin autograft, three-dimensional skin construct, and/or other wound care regimens.

Wounds after surgery are also treated by the compositions of the invention. Surgery includes, but is not limited to non-cosmetic, cosmetic, plastic and/or reconstructive surgery procedures.

Cosmetic, plastic and reconstructive surgery procedures include, but are not limited to breast lift, breast augmentation or reduction, facelift, forehead lift, surgery of the nose, surgery of the ear, surgery of the eye lid, surgery of the abdomen, liposculpturing, liposuction, scar revision, fat transfer, soft-tissue augmentation, cryosurgery or cryotherapy, hair transplantation, nail surgery, sclerotherapy, laser surgery, tattoo removal and/or vein surgery.

In addition, skin conditions, disorders or diseases treated by the said compositions comprise non-pathologic skin conditions including, but not limited to, normal skin and/or healthy skin, intrinsically and/or extrinsically aged or photoaged skin. Furthermore, skin conditions, disorders or diseases treated by the said compositions comprise skin exposed (in contact with) to cosmetic products, pharmaceutical or dermatological products, household products, industrial products and/or products containing ingredients harmful for skin such as corrosive chemicals, skin irritants and skin allergens.

Cosmetic and/or dermatological products include, but are not limited to products containing one or more exfoliant, keratolytic, wart remover, hair remover, chemical peel, physical peel, self-tanning ingredient, fragrance, deodorant, anti-dandruff active, anti-acne active, anti-inflammatory agent, anti-rosacea active, make-up cosmetic, dye, color additive, pigment, skin lightener, skin whitening agent, antioxidant, lipid, skin nutrient, sunscreen, surfactant, polymer, protein, myorelaxant, anti-aging ingredient, anti-wrinkle agent, moisturizer, humectant, vitamin, emollient, film-forming agent, liposome, nanoparticule, microparticule, nanosphere, microsphere and/or any possible mixtures and combinations thereof.

The said cosmetic and/or dermatological products may comprise one or a combination of the following ingredients: fruit acids, alpha-hydroxy acids, beta hydroxyl acids, azelaic acid, benzoic acid, benzoyl peroxide, betamethasone, clindamycin, corticosteroids, diclofeneac, dithranol, fluorouracil, hydrocortisone, hydrocortisone acetate, hydroquinone, indomethacin, isotretinoin, kojic acid, metronidazole, phenol, retinoic acid, retinol, retinaldehyde, retinoyl beta-glucuronide, salicylic acid, selenium sulfide, sodium sulfacetamide, sulfur, tazarotene, tretinoin, trichloroacetic acid, urea, fatty acids, fatty acid esters, vitamins A, B, C, D, E, F, H and K as well as any derivatives thereof.

Alpha-hydroxy acids include but are not limited to glycolic acid, lactic acid, malic acid, citric acid, glycolic acid combined with ammonium glycolate, alpha-hydroxyethanoic acid combined with ammonium alpha-hydroxyethanoate, alpha-hydroxyoctanoic acid, alpha-hydroxycaprylic acid, hydroxycaprylic acid, mixed fruit acid, tri-alpha hydroxy fruit acids, triple fruit acid and sugar cane extract.

In one of the preferred embodiments of this invention, the said compositions are used to treat skin and/or skin conditions occurring from cosmetic and/or dermatological procedures. Cosmetic and/or dermatological procedures include, but are not limited to light chemical peels, medium chemical peels, deep chemical peels, physical peels, waxing, microdermabrasion, dermabrasion, light treatments (intense pulse light, photomodulation, treatments with visible, non-visible, infrared and/or ultraviolet light), laser treatments, radiofrequency treatments, thermal treatments (heat, cold, cycles of heat and cold), electrical treatments, sonnication treatments, mechanical treatments (massage, pressure, suction, vibration, friction, abrasion), oxygen and/or ozone treatments, injections and/or any combinations thereof. The said compositions are used in combination with said cosmetic and/or dermatological procedures; either before, after and/or during (in parallel) the cosmetic and/or dermatological procedures.

Household and/or industrial products include, but are not limited to soaps, detergents, shampoos, cleansing products, hand washing products, paints, epoxy hardeners, organic solvents, acids, bases, metals, hot or cold liquids and hot or cold materials or instruments.

Unless otherwise stated, the following terms used in the specification and claims have the meanings given below:

The terms "treated", "treatment" or "therapy" and the like refer to changes in the recipient's status. The changes can be either subjective or objective and can relate to features such as symptoms, signs or appearance of the disease or condition being treated. For example, if the patient or/and subject notes decreased itching or decreased pain, then successful treatment has occurred. Similarly, if the clinician notes objective changes, such as by histological analysis of a biopsy sample, then treatment has also been successful. Alternatively, the clinician may note a decrease in inflammatory lesions or other abnormalities upon examination of the patient. This would also represent an improvement or a successful treatment. Prevention of deterioration of the recipient's status is also included by the term. Therapeutic benefit includes any of a number of subjective or objective factors indicating a response of the condition being treated as discussed herein.

The terms "drug", "pharmacological agent", "pharmaceutical agent", "active", "agent" and "active agent" and the like are used interchangeably and are intended to have their broadest interpretation as to any therapeutically active substance which is delivered to a living organism to produce a desired, usually beneficial effect. In general, this includes therapeutic agents in all of the major therapeutic areas, also including proteins, peptides, oligonucleotides, and carbohydrates as well as inorganic ions.

Skin Conditions, Disorders and/or Diseases

The compositions of the invention designed for treating a subject suffering from a skin condition, disorder and/or disease comprise one or more fetal skin cell proteins obtained from one or more fetal skin cells by induced cell lysis. The invention discloses a method preparing a composition comprising one or more fetal skin cell proteins mixed, integrated or combined with a carrier suitable for topical, mucosal, ocular, rectal and vaginal application.

The composition can be used to treat a variety of inflammatory, neurogenic and/or neuroinflammatory skin conditions, disorders or diseases such as vulvodynia, vulvar vestibulitis, vulvar lichen sclerosus, atopic dermatitis or eczema, hand eczema, seborrheic dermatitis, rosacea, psoriasis, localized and/or generalized pruritus, photo-dermatoses and/or sunburns and radio-dermatitis.

The composition can be further used to treat acute and chronic wounds such as minor burns, minor wounds, crevices, cracks, scratches, accidental wounds, ulcers, peri-ulcer skin, skin after wound closure and/or healing due to standard wound regimens and/or atrophie blanche.

The composition can be also to used to improve appearance (or embellish) the skin or skin conditions after cosmetic and/or dermatological procedures including but not limited to light chemical peels, medium chemical peels, deep chemical peels, physical peels, waxing, microdermabrasion, dermabrasion, light treatments (visible, non-visible, infrared, ultraviolet), laser treatments, radiofrequency treatments, thermal treatments (heat, cold, cycles of heat and cold), electrical treatments, sonnication treatments, mechanical treatments (massage, pressure, suction, vibration, friction, abrasion), oxygen and/or ozone treatments, injections, cosmetic surgery and/or any combinations thereof. The said compositions are used in combination with said cosmetic and/or dermatological procedures; either before, after and/or during (in parallel) the cosmetic and/or dermatological procedures.

In addition, the compositions can be used to prevent and/or improve appearance of scars and/or keloids. Also, the composition can be used to hydrate or moisturize skin, in particular dry skin or xerotic skin due to xerosis.

A brief, but incomplete description of the skin conditions, disorders or diseases treated by the composition of this invention is given in the next paragraphs. More detailed and regularly updated information about the symptoms, diagnosis and treatments of the skin conditions, disorders or diseases can be found in standard textbooks on veneorology, andrology, wound healing, dermatology and/or cosmetics such as 'Fitzpatrick's Dermatology in General Medicine" ($5^{th}$ edition; edited by I. M. Freedberg, A. Z. Eisen, K. Wolff, K. F. Austen, L. A. Goldsmith, S. I. Katz and T. B. Fitzpatrick) and 'Textbook of Cosmetic Dermatology' ($2^{nd}$ edition; edited by R. Baran and H. I. Maibach) which are specifically incorporated herein by reference.

Inflammatory Skin Conditions

A large number of skin conditions, disorders or diseases including, but not limited to acne, atopic dermatitis, allergic contact dermatitis, atrophie blanche, dandruff, dermatitis, hand dermatitis or hand eczema, dermatitis herpetiformis, diaper rash, eczema, generalized exfoliative dermatitis, keloid formation, localized or generalized pruritus, photo-dermatoses, peri-ulcers, psoriasis, sebaceous cyst, seborrheic dermatitis, rosacea, vulvodynia, vulvar vestibulitis or vulvar vestibulitis syndrome, vulvar lichen sclerosus fall into the category of inflammatory, neurogenic and/or neuroinflammatory skin condition, disorder or disease.

Vulvar vestibulitis syndrome is on of the most common subtype of vulvodynia. It is a complex feminine disease involving pain limited to the vulvar vestibule without objective clinical findings to explain the symptoms. The hallmark of vulvar vestibulitis syndrome is the character of localized pain confined to the vulvar vestibule and its elicitation in response to touch or pressure. In this respect, it differs from dysesthetic vulvodynia, which involves chronic, often non-localizes vulvar pain that occurs with or without stimulation.

According to Friedrich (J Reprod Med 32, 1987, 110-114), the symptoms of VVS are localized to the vulvar vestibule. The criteria for recognizing VVS include: (1) pain on vestibular touch or attempted vaginal entry, (2) tenderness in response to pressure localized within the vulvar vestibule; and (3) physical findings confined to vestibular erythema of various degrees (J Reprod Med 32, 1987, 110-114). The erythema may be diffuse or focal, and may be localized around the orifices of the vestibular glands or at the fourchette. Other causes for vestibular erythema and tenderness, such as candidiasis (yeast infections) or herpes infections should be excluded (Smart and MacLean: Curr Opin Obstet Gynecol 15, 2003, 497-500).

VVS may be acute or chronic, whereas an arbitrary cutoff of six months to distinguish between the two forms is most accepted. The causes of VVS are multi-factorial. Fungal or bacterial infections (e.g: candida), chemical irritants (e.g: soaps), therapeutic agents (e.g.: antiseptics, suppositories, creams), and allergic drug reactions are suspected causes of the acute form. In the acute form, treatment of the presumed cause may lead to rapid relief.

The condition significantly impairs sexual function and creates significant psychological distress. Besides pain, which is described as sharp, burning, or a sensation of rawness, other symptoms include itching, swelling and abrasion. In severe cases, pain may prohibit sexual intercourse. In addition, tampon insertion, biking, or wearing tight pants may also elicit discomfort. Morbidity extends therefore often beyond the local symptoms and many women may experience secondary sexual dysfunction and often under-recognized depression. These changes can include profound adverse effects on marriages.

Vulvar vestibulitis syndrome was recently reviewed by Farage M. A. and Galask R. P. in Eur J Obstet Gynecol Reprod Biol ("Vulvar vestibulitis syndrome: A review", May 28, 2005, Epub ahead of print), which is included as reference herein.

The prevalence of vulvar vestibulitis syndrome in the general population is unknown. The prevalence was 15% among patients seen over a six-month period at a gynecologic clinic (Br J Obstet Gynaecol 1991, 98, 703-706). The only available population based survey, which comprised 4915 women aged 18 to 64 from ethnically diverse Boston communities (response rate 68%), found that approximately 16% of respondents reported histories of chronic burning, knife like pain, or pain on contact that lasted for at least 3 months or longer (J Am Med Womens Assoc 2003, 58, 82-88). Nearly 7% were experiencing the problem at the time of the survey. About 12% complained specifically of pain on vulvar contact. In addition, the survey found that nearly 40% of women with vulvar pain chose not to seek treatment, and of those who did, 60% saw 3 or more doctors, many of whom could not provide a diagnosis. However, the survey does not fully distinguish between vulvar vestibulitis and dysesthetic vulvodynia.

The etiology of vulvar vestibulitis syndrome is not yet established. A perplexing array of variables has been associated with the condition, suggesting a multi-factorial pathogenesis (Farage M A and Galask R P). The prevailing theory is that vulvar vestibulitis syndrome is a neuropathic disorder involving abnormal pain perception possibly resulting from sensitization of vestibular nerve fibers and the establishment of a sympathetically maintained pain loop. In this theory, unidentified trigger elements;—presumably some form of chronic inflammation—, activate and cause prolonged firing of the sympathetic Type C nerve fibers responsible for transmitting noxious chemical stimuli to the brain. This causes the wide dynamic range neurons in the brain to respond abnormally, such that mild stimuli are perceived as pain. The process has been suggested to first result in the localized pain of vulvar vestibulitis syndrome then progress to chronic, generalized vulvar pain of dysesthetic vulvodynia.

Several studies support the neuropathic etiology for vulvar vestibulitis syndrome: threshold to thermal and mechanical stimuli are lowered in vulvar vestibulitis patients (Pain. 2004, 107, 47-53), while recent lines of evidence highlight a potential genetic disposition to chronic inflammation among vulvar vestibulitis patients. Pro-inflammatory variants of the polymorphic interleukin-1 receptor antagonist gene (Am J Obstet 182: 2000, 283-285) and melanocortin-1 receptor gene (J Reprod Med 2004, 49, 503-509) are substantially more prevalent in vulvar vestibulitis afflicted women. Notably, a marked reduced induction of interleukin-1 receptor antagonist was observed in the blood of vulvar vestibulitis patients compared to healthy controls (Am J Obstet Gynecol 2002, 186, 696-700). Separately, a deficiency in interferon-α, unrelated to the above-mentioned genotypes, may contribute to chronic vestibular inflammation in a subset of vulvar vestibulitis patients by reducing their ability to combat intracellular infection (Am J Obstet Gynecol 2002, 186, 361-364).

Possible triggers for vulvar vestibulitis syndrome include infectious agents, excessive use of irritating topical products or medications, prior laser or cryogenic treatments of HPV infection, or hypersensitivity to seminal fluid. A complicating factor in identifying these triggers is the delay between first onset of symptoms and first diagnosis (Farage M A and Galask R P).

VVS can be very difficult to treat, due to its multiple and frequently unknown causes. Patients sometimes suffer through a period of misdiagnosis, and may present with a long history of unsuccessful attempts at therapy. The first-line therapy for vulvar vestibulitis is the treatment of its suspected causes. This includes the discontinued use of the irritants and therapeutic agents, local and systemic that may contribute to the problem.

No accepted curative therapy exists and current treatments lack clear etiologic basis (Farage M A and Galask R P). Little rigorous, randomized prospective clinical trials exist for most therapies; evidence for their efficacy derives largely from single case studies or case series. Studies also differed in the definition of success criteria, including the endpoints assessed, the extent of recovery and the duration of follow-up. Interventions include; symptom relief (topical anesthetics such as lidocaine, low dose tricyclic antidepressants such as amitriptyline, gabapentin, etc.), biofeedback (electromyographic biofeedback of pelvic floor musculature), pharmacological treatment of putative infectious causes (oral fluconazole, injectable interferon-α or -β, etc.), psychosocial and supportive therapies (cognitive-behavioral, sex therapy, etc.), surgery to remove afflicted vestibular tissue (vestibuloplasty, vestibulectomy, perineoplasty), and combinations thereof.

No single treatment works in all patients. Moreover, many of these approaches involve complex medical procedures, significant costs, and/or undesirable side effects.

There is a need for improved methods for treating vulvar vestibulitis, especially those cases of unknown etiology and those cases that fail to respond to the treatment of suspected causes.

Lichen sclerosus is a poorly recognized chronic inflammatory skin disorder which mainly affects the vulval and perianal area (Am J Clin Dermatol. 2004: 105-25). Although it is considered a condition which mainly affects mature women, there are women of all ages with lichen sclerosus. Men can have the disorder and this affects the penis and sometimes the anal area. Children can also suffer from lichen sclerosus and it can sometimes affect other areas of the body. When lichen sclerosus affects areas of the body other than the genitals, it is know as "extra genital lichen sclerosus". It is not known what causes lichen sclerosus but it has been found that there is a connection between lichen sclerosus and thyroid disease, vitiligo and other auto-immune diseases.

The different symptoms are chronic itching and soreness of the vulval area and pain, splitting of the vulval skin, causing stinging and pain, inflammation and sometimes swelling, splitting and bleeding of the skin around the anal opening when passing bowel motions, causing pain and discomfort, the skin becomes fragile and pale and white in appearance and there is an increased susceptibility to infection and thrush, "shrinking" (atrophy) of the vulva area, change in shape and size of the area, sometimes causing urination difficulties and sexual problems, lichen sclerosus does not extend into the vagina, and/or in men the foreskin becomes "fused" or tight making retraction of the foreskin painful and urination may become difficult.

Diagnosis can be a difficult and long process. Many general practitioners are unable to recognize the symptoms and patients are sometimes misdiagnosed and treated for "thrush", STDs, menopause, or hormonal problems. Referral to a specialist is usually necessary and a skin biopsy is taken to establish the presence of lichen sclerosus and rule out any possibility of malignancy.

In women, lichen sclerosus falls under the general category of vulvodynia.

Psoriasis is a persistent skin disease that received its name from the Greek word for "itch." The skin becomes inflamed, producing red, thickened areas with silvery scales; most often on the scalp, elbows, knees, and lower back. In some cases, psoriasis is so mild that people do not know they have it. At the opposite extreme, severe psoriasis may cover large areas of the body.

The cause of psoriasis is unknown. However, recent discoveries indicate that it is a chronic inflammatory disorder of the skin that is mediated by T-cells, dendritic cells and inflammatory cytokines (Nat Rev Immunol. 2005, 5: 699-711). Because of the inflammation, the skin sheds too rapidly, every three to four days. People often notice new spots 10 to 14 days after the skin is cut, scratched, rubbed, or severely sunburned. Psoriasis can also be activated by infections, such as strep throat, and by certain medicines. Flare-ups sometimes occur in the winter, as a result of dry skin and lack of sunlight.

Psoriasis comes in many forms. Each differs in severity, duration, location, and in the shape and pattern of the scales. The most common form begins with little red bumps and gradually these areas grow larger and scales form. While the top scales flake off easily and often, scales below the surface stick together. When they are removed, the tender, exposed skin bleeds. These small red areas then grow, sometimes becoming quite large. Elbows, knees, groin and genitals, arms, legs, palms and soles, scalp and face, body folds and nails are the areas most commonly affected by psoriasis. It will often appear in the same place on both sides of the body.

Nails with psoriasis have tiny pits on them. Nails may loosen, thicken or crumble and are difficult to treat. Inverse psoriasis occurs in the armpit, under the breast and in skin folds around the groin, buttocks, and genitals. Guttate psoriasis usually affects children and young adults. It often shows up after a sore throat, with many small, red, drop-like, scaly spots appearing on the skin. It often clears up by itself in weeks or a few months. Up to 30% of people with psoriasis may have symptoms of arthritis and 5-10% may have some functional disability from arthritis of various joints. In some people, the arthritis is worse when the skin is very involved. Sometimes the arthritis improves when the condition of the patient's skin improves.

Rosacea is a common chronic cutaneous disease primarily of the facial skin. It is common in the third and fourth decade of life, peaking at the age of 40 and 50 years. The pathophysiology of rosacea appears to be inflammatory, and most of the interventions modulate the inflammatory process in some way (Cutis. 2005, 75(3 Suppl): 27-32). Topical agents include various formulations of sodium sulfacetamide and sulfur, metronidazole, azelaic acid, and benzoyl peroxide/clindamycin. Oral agents include antibiotics in conventional and sub-antimicrobial doses. A paradigm shift in progress in the management of rosacea encompasses the use of these and other agents either alone or, increasingly, in different combinations, based on the subtype of rosacea.

The early stage rosacea is characterized by persistent erythema and teleangiectasia predominantly of the cheeks frequently followed by papules and papulopustules. Later, there may occur diffuse hyperplasia of connective tissue and sebaceous glands. This can cause a hypertrophy of the nose, a so called rhinophyma. Rosacea occurs in stages and may effect the eyes, most commonly resulting in blepharitis and conjunctivitis. Also other parts beside the face such as retroauricular areas, neck, chest, back and the scalp may be affected. The clinical appearance can be similar to acne, but in contrast rosacea is not a primary follicular disease. In America, an estimated 14 million Americans are affected. Because of its red-faced, acne-like effects on personal appearance, it can cause significant psychological, social and occupational problems if left untreated.

Dermatitis represents an inflammation of the skin. Dermatitis actually refers to a number of skin conditions that inflame the skin. Dermatitis is characterized by skin that may be red, swollen, blistered, scabbed, scaly, oozing, or itchy. Some types of dermatitis are caused by allergies, while the majority does not have any known causes. There are many types of dermatitis that require clinical care by a physician or other healthcare professional.

Atopic dermatitis (atopic eczema or just eczema) is a heterogeneous group of different non-infectious skin diseases which may be caused by irritative as well as immune mechanisms and lead to pathological changes in the epidermis and upper dermis. It is the most common category of skin diseases. Eczematous disorders are also frequent occupational diseases. Eczema is a constellation of clinical findings, not a particular disease, and may manifest with erythema, papules, vesicles, crusts, weeping and edema in its acute phase and with thickening of the skin, lichenification, and scaling in its chronic phase. Itching is a guiding symptom. The terms "dermatitis" and "eczema" are often used interchangeably, whereas some authors use the term "dermatitis" for describing acute inflammatory lesions and the term "eczema" for rather chronic epidermal lesions with hyperkeratosis. Both terms are often used synonymously, although one should be aware of the fact that the term "dermatitis" may also be used in non-eczematous diseases (such as dermatitis herpetiformis Duhring).

Hand dermatitis (hand eczema) is common. Hand rashes usually result from a combination of sensitive skin and irritation or an allergic reaction from materials touched. People with hand dermatitis often have dermatitis elsewhere.

Contact dermatitis is a physiological reaction that occurs after skin comes in contact with certain substances. About 80 percent of these reactions are caused by irritants to the skin. The remaining 20 percent of reactions are caused by allergens, which trigger an allergic response. In allergic reactions, the reaction may not be immediate, but may start after several days. Contact dermatitis caused by an irritant that is not an allergic response occurs from direct contact with the irritant.

The most common causes of allergic contact dermatitis in adults and children include the following: soaps, detergents, perfumes, diapers, different foods, harsh baby lotions, plants, as well as metals, cosmetics, and medications may also cause a contact dermatitis reaction. Poison ivy, which is part of a plant family that includes poison oak and sumac, is one of the most common causes of a contact dermatitis reaction. Several thousand chemical agents are capable of causing allergic contact dermatitis. Nickel, chrome, and mercury are the most common metals that cause contact dermatitis. Nickel is found in costume jewelry, belt buckles, and wristwatches, as well as zippers, snaps, and hooks on clothing. Many types of cosmetics can cause allergic contact dermatitis. Permanent hair dyes that contain para-phenylenediamine or derivatives thereof are the most frequent causes. Other products that may cause problems include semi-permanent hair dyes or dyes used in clothing, perfumes, eye shadow, nail polish, lipstick, and some sunscreens. Neomycin, which is found in antibiotic creams, is the most common cause of medication contact dermatitis. Penicillin, sulfa medications, and local anesthetics, such as novocaine or paraben, are other possible causes.

The most common symptoms of contact dermatitis may include: mild redness and swelling of the skin, blistering of the skin, itching, scaling and temporary thickening of skin. The most severe reaction is at the contact site. The symptoms of contact dermatitis may resemble other skin conditions. However, each individual may experience symptoms differently.

Dermatitis herpetiformis is an intensely pruritic (itchy) skin disease characterized by eruptions of clusters of small blisters or vesicles (small elevations of the skin containing fluid) and small bumps or papules (small, solid, elevations on the skin). Dermatitis herpetiformis mostly affects people between 15 and 60 years of age. Dermatitis herpetiformis is related to the presence of IgA deposits under the skin. These deposits occur in response to consuming glutens (proteins) in the diet, such as those found in wheat, barley, rye, and oat products. However, once IgA deposits occur, they are slowly cleared by the body even when the individual is gluten free. The disease is not common among African-Americans or Asians. People with dermatitis herpetiformis often have a high incidence of autoimmune disorders and thyroid disease.

The most common symptoms of dermatitis herpetiformis may include: clusters of itchy, small blisters, mostly on the elbows, lower back, buttocks, knees, and back of the head, itching and burning are often severe. Most individuals will also have some damage to their intestines.

The symptoms of dermatitis herpetiformis may resemble other skin conditions. However, each individual may experience symptoms differently.

Generalized exfoliative dermatitis is a severe inflammation of the entire skin surface due to a reaction to certain drugs, or as a result of complications from another skin condition. In some cases, lymph node cancer (lymphoma) can cause generalized exfoliative dermatitis. Often, however, no cause can be found.

The following are the most common symptoms of generalized exfoliative dermatitis. However, each individual may experience symptoms differently. Symptoms may include: extreme redness of the skin, scaling, thickened skin, itching, swollen lymph nodes, fever, loss of fluids and proteins through the damaged skin. The symptoms of generalized exfoliative dermatitis may resemble other skin conditions.

A sebaceous, or epidermal cyst, is a small, movable lump under the skin that appears when surface skin cells move deeper within the skin and multiply. These cells form the wall of the cyst and secrete a soft, yellowish substance, which fills the cyst. If the wall is ruptured, this material is discharged into the surrounding skin, which causes irritation and inflammation. Sebaceous cysts often appear on the scalp, face, ears, back, or groin area. A sebaceous cyst may be a blocked gland or duct.

Seborrheic dermatitis is an inflammation of the upper layers of skin, characterized by red, itchy skin that sheds scales. A hereditary condition, seborrheic dermatitis is often aggravated by cold weather conditions. Seborrheic dermatitis is common during infancy. In infants, the condition is also called "cradle cap," because of its characteristic scaly appearance on the scalp. However, cradle cap can also occur in the diaper area. Seborrheic dermatitis in this age group usually clears up on its own within the first year. When seborrheic dermatitis occurs at middle age, the condition is usually more intermittent. And, when seborrheic dermatitis occurs at old age, the condition is usually more intermittent. People with oily skin or hair are also more at risk for developing seborrheic dermatitis.

Symptoms associated with seborrheic dermatitis may include: itching scalp, dry or greasy scales on the scalp, a yellow or red scaly rash along the hairline, behind the ears, in the ear canal, on the eyebrows, around the nose, and/or on the chest. The symptoms of seborrheic dermatitis may resemble other skin conditions. However, each person may experience symptoms differently.

Acne is a skin condition, which has plugged pores (blackheads and whiteheads), inflamed pimples (pustules), and deeper lumps (nodules). Acne occurs on the face, as well as the neck, chest, back, shoulders, and upper arms. Acne can be disfiguring and upsetting to the patient. Untreated acne can leave permanent scars. To avoid acne scarring, treating acne is important.

Keloids are erythematous, tender, elevated, hyperpigmented, firm to rock hard in consistency and variably pruritic because of their mast cell content. Keloids are benign fibrous growths which occur more commonly among the darker pigmented races. A keloid scar must have persisted for more than 12 months, and have margins extending beyond the confines of the original wound. Keloids occur from such skin injuries as surgical incisions, traumatic wounds, vaccination sites, burns, chickenpox, acne, or even minor scratches. They may become irritated from rubbing on clothing or other forms of friction.

During the early phases of wound healing, extracellular matrix is deposited while collagen and proteoglycans are accrued by fibroblasts. In normal skin or in a mature scar, the rate at which fibroblasts accumulate collagen and proteoglycans diminishes with time. However, in keloid scars, the process of wound healing continues at an accelerated rate, with over-reactive proliferation of fibroblasts continuing for weeks or months. The pathogenesis of keloid formation is still not entirely understood, but it has been postulated that cytokines such as interleukin-1 and transforming growth factor-beta could be responsible for changing collagen metabolism, thereby leading to keloid formation, namely, that the neovascular endothelial cells express transforming growth factor-beta, with subsequent production of TGF-beta by adjacent fibroblasts. The expression of type I and VI collagen genes is also enhanced in keloidal tissue.

Pruritus is the medical word for itch. It is defined as a sensation that provokes the desire to scratch. Itching can be a significant source of frustration and discomfort for patients. The exact cause of an itch is unknown and is a complex process. Ultimately it involves nerves in the skin responding to certain chemicals such as histamine, and then processing these signals in the brain. Pruritus can be a symptom of certain skin diseases, and sometimes a manifestation of an internal process. In other patients where there is no evidence of skin or internal disease, pruritus may be due to faulty processing of the itch sensation within the nervous system.

There are many skin conditions, disorders or diseases that may have itching associated with a rash as a prominent symptom. Examples would be hives, but are not limited to, chicken pox, and eczema. Some skin conditions only have symptoms of pruritus without having an apparent rash. Dry skin, for example, is very common in the elderly, and can really itch (especially in the winter), with no visual signs of a rash. Pruritus is usually secondary to subtle dry skin, but it may be a manifestation of an internal condition. Insect bites and some parasitic infestations of the skin, such as scabies and lice, may be very itchy.

Acute and Chronic Wounds

Wounds (i.e., lacerations, opening, or ulcers) can be either acute or chronic. Acute wounds are typically sharp injuries to the skin involving little tissue loss. Most acute wounds are closed and are healed by bringing the wound edges together. Chronic wounds are wounds that fail, or are slow, to heal completely. Examples of chronic wounds include pressure sores (decubitus ulcers), diabetic skin ulcers, venous stasis ulcers, burn injury and defects arising following tumor excision.

The cellular morphology of a wound consists of three distinct zones: a central wound space, a gradient zone of local ischemia, and an area of active collagen synthesis. Despite the need for more rapid healing of wounds (i.e., severe burns, surgical incisions, lacerations and other trauma), to date there has been only limited success in accelerating wound healing with pharmacological agents.

The primary goal in the treatment of wounds is to achieve wound closure. Open cutaneous wounds represent one major category of wounds, which includes acute surgical and traumatic wounds, e.g., chronic ulcers, burn wounds, as well as chronic wounds such as neuropathic ulcers, pressure sores, arterial and venous (stasis) or mixed arterio-venous ulcers, and diabetic ulcers. Typically, these wounds heal according to the following process: i) inflammation, ii) fibroblast proliferation, iii) blood vessel proliferation, iv) connective tissue synthesis, v) epithelialisation, and vi) wound contraction. Wound healing is impaired when these components, either individually or as a whole, do not function properly. Factors that can affect wound healing include malnutrition, infection, pharmacological agents (e.g., cytotoxic drugs and corticosteroids), diabetes, and advanced age (Current Surgical Diagnosis & Treatment, Way; Appleton & Lange, 1988, 86-98).

Many different products and protocols are available to treat chronic wounds (as illustrated in Brit J Plast Surg 55: 2002, 185-193). These include simple bandages (notably compression bandages), foams and films, gels and colloids, and pharmaceutical products, such as growth factors. Typically wound healing with a moist occlusive dressing is used rather than using dry, non-occlusive dressings (Nature 193: 1962, 293-294). Today, numerous types of dressings are routinely used in wound healing. These include films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), and cellophane (cellulose with a plasticizer) (Dermatol Surg 21: 1995, 583-590; Burns 10: 1983, 94). Certain types of wounds (e.g., diabetic ulcers, pressure sores) and the wounds of certain subjects (e.g., recipients of exogenous corticosteroids) do not heal in a timely manner (or at all) with the use of these wound dressings.

Research has shown that the majority of ulcers can be induced to heal by the application of adequate levels of sustained graduated compression. For patients with venous disease, the application of graduated external compression, by forcing fluid from the interstitial spaces back into the vascular and lymphatic compartments, can help to minimize or reverse skin and vascular changes attributed to blockage or damage to the venous system.

Additionally, several pharmaceutical modalities (e.g., administration of zinc sulfate, vitamins A, C, and D, calcium, magnesium, copper and iron), have also been utilized in an attempt to improve wound healing. However, except in very limited circumstances, the promotion of wound healing with these agents has met with little success.

There are three types of bandages that are commonly used: (1) lightweight conforming-stretch bandages, (2) light support bandages, and (3) compression bandages including light, moderate, high and extra-high performance compression bandages.

In severely burned patients who have little or no remaining intact skin, artificial skin constructs or cellular bandages are used to cover and protect the wounded area, but that also promotes re-growth of a natural skin rather than of scar tissue. Examples of such artificial skin constructs are Apligraf™, Trancyte™ or Ortec™.

Cosmetic and Dermatological Procedures

Chemical peels (also called chemexfoliation or dermapeeling) consists in the application of a chemical solution to remove the outer layer of skin to treat fine lines, wrinkles, mild scarring, acne, skin discoloration, and pre-cancerous growths. Peeling solutions may include one or more chemicals such as alpha-hydroxy acids, beta-hydroxy acids, fruit acids, salicylic acid, Jessner's solution, trichloroacetic acid, phenol, or carbolic acid. The immediate after-effect of a chemical peel is similar to sunburn. After a mild or superficial peel, redness and scaling of the skin last 3 to 5 days. Medium-depth or deep peeling can result in redness, swelling, blistering and peeling for 7 to 14 days. Medications are prescribed to alleviate discomfort. Overexposure to sun must be avoided for a period of time to prevent sun damage while the new skin is susceptible to injury.

Dermabrasion consists in a surgical sanding or planning (by movement of at high speed rotating wire, brushes, diamond fraises, serrated wheels, etc.) of the outer layer of skin to improve acne and other scars, remove tattoos and minimize age spots, wrinkles and certain types of skin growths. Post-treatment wound care is required, whereas re-epithelialisation is usually complete in about 10 days. The principal after-effects are redness of the skin similar to a severe sunburn, hypertrophic scar or keloid formation, post-inflammatory hyper-, or hypopigmentation. Patients must avoid sunlight for 3 to 6 months after treatment.

Microdermabrasion is a less invasive facial rejuvenation treatment that uses micro-particles to abrade and rub off the top skin layer, vacuuming out the particles of dead skin. It may be repeated at intervals. Potential after-effects are redness of the skin similar to severe sunburn.

Light and/or laser treatments comprise many applications for skin resurfacing and skin rejuvenation, removal of age spots, hair, scars, tattoo and warts, as well as for the treatment of acne, birthmarks, port wine stains, psoriasis, rosacea, stretch marks, veins, vitiligo and other skin conditions including actinic keratosis and skin cancer.

They may be ablative (injure and "ablate" surface) or non-ablative (non-wounding). Ablative laser treatments ($CO_2$, Er:YAG, Argon, etc.) require post-treatment wound care, whereas re-epithelialisation is usually complete in about 10 days. Erythema typically endures for up to 3 to 4 months and the skin may stay sensitive over months. Risk of hypertrophic scar or keloid formation, post-inflammatory hyper-, or hypopigmentation exists.

Non-ablative lasers (laser with cooling, long pulsed laser, Fraxel laser, etc) or light treatments (intense pulse light (IPL) treatments, photomodulation, infrared light, etc.) are less invasive since they target the lower layers of skin (dermis) and leave the epidermis mostly unharmed. Side effects are redness and skin sensitivity or minimal swelling for some time.

An alternative to laser skin resurfacing is electrosurgical resurfacing, also called "cold ablation." This technique uses a micro-electrical radio frequency to deliver a pulse of energy to the skin, removing or improving superficial to moderate skin damage. The procedure has few after-effects, and recovery from mild to moderate swelling is usually complete within a month. Electrosurgical resurfacing offers the advantage of being applicable to most skin types and colors, without loss of skin pigmentation.

Removal of superfluous hair may contribute to overall improved appearance, with or without concomitant facial skin rejuvenation. Traditional methods of dealing with superfluous hair include: (1) bleaching with hydrogen peroxide to make the hair less visible, (2) shaving to temporarily remove hair, (3) plucking hairs, (4) coating the skin with wax, then removing hair with the waxy coat, (5) using a chemical depilatory to "dissolve" unwanted hair, and (6) electrolysis or electrothermolysis to destroy hair follicles for relatively permanent hair removal. Chemical depilation of facial skin may be irritating. Laser hair removal in most current use is accomplished by photothermolysis. Side effects of laser hair removal include post-treatment pain for a few hours to a few days, and skin redness.

Other cosmetic and dermatological procedures include:

Ambulatory phlebectomy: Removal of undesired varicose and spider leg veins via a series of tiny incisions along the path of an enlarged vein.

Blepharoplasty: Upper and lower eyelid surgery to remove loose skin and excess fatty tissue.

Botulinum toxin: Botulinum toxin injection therapy is used to paralyze certain facial muscles which cause frown lines, crow's feet and other wrinkles. It also is used to improve neck lines and control excessive sweating. As an alternative to botulinum toxin, botulinum toxin-like substances may be used.

Cosmetic surgery: Aesthetic procedures to improve and rejuvenate the appearance of the skin, e.g., laser resurfacing, wrinkle fillers, liposuction, chemical peeling, and hair restoration, etc.

Cryosurgery or cryotherapy: Freezing the skin tissue with liquid nitrogen to remove skin growths, age spots or warts.

Curettage and desiccation: Use of a sharp instrument to scrape away skin tissue, followed by application of a heated electric needle to destroy skin growths.

Flap surgery: Transfer of adjacent skin tissue, often used to move hair-bearing skin to cover balding areas of the scalp.

Injection of fillers: Fillers are materials (such as collagen, hyaluronic acid, calcium hydroxylapatite, poly L-lactic acid, silicon, etc.) that are placed or injected into deeper lines and wrinkles. Filler agents typically are used for those wrinkles that are too deep to be treated with lasers. Most commonly filler agents are used for smile lines wrinkles, between the eyebrows, sagging cheekbones or to enhance the appearance of upper and lower lips. Acne, chicken pox and other depressed scars can also be improved.

Hair restoration surgery: A variety of techniques, such as punch transplanting, mini- and micro-grafts, scalp reduction and skin flaps, to correct baldness and restore a person's natural hairline.

Liposuction: Liposuction is the removal of excess fat with a small, straw-like instrument called a cannula that is attached to a suction machine. The use of tumescent liposuction allows dermatological surgeons to safely and effectively remove deep and superficial layers of undesired fat under local anesthesia.

Microlipoinjection: A form of soft tissue augmentation using one's own fat to fill and contour wrinkles, folds and depressions resulting from aging, sun-damage, injury or surgery.

Micropigmentation: A permanent method of implanting pigment into the skin to add color for the treatment of vitiligo, skin grafts or burn scars and for cosmetic purposes.

Mohs micrographic surgery: Precise removal of skin cancer layer by layer with the aid of a microscope.

Nail surgery: Removal or repair of a nail abnormality for the purposes of diagnosis and/or treatment.

Sclerotherapy: Injection of a solution to remove unwanted varicose and spider leg veins.

Soft tissue fillers: Filler substances are generally used to "plump up" and minimize wrinkles, furrows and hollows in the face, giving the skin a smoother and more pleasing appearance. They can be injected under the skin. Fillers such as bovine collagen and related materials, one's own fat and polymer implants are effective for contouring specific facial sites and correcting depressions and scars.

Xerosis or Dry Skin

Xerosis is the medical term for dryness of the skin. This is a common problem in colder climates. When cold, dry air is artificially heated it becomes even dryer, acts almost like a sponge, and "pulls" water from the skin through enhanced surface evaporation. Since water is the main "softener" of the skin, dry skin may become rough, scaly, and eventually red, inflamed, and itchy. In severe cases these changes will have the appearance of dermatitis. The treatment "winter itch" is to 1) increase the relative humidity of the air; 2) decrease factors that may exacerbate the problem, such as excessive bathing and the use of harsh soaps; and 3) moisturize the skin with emollient creams, lotions, or ointments.

Fetal Skin Cell Protein Preparation

Induced cell lysis (induced cell disruption) of fetal skin cells, which are obtained at the age of gestation where fetal skin heals with no or little scar-formation after wounding, provides fetal skin cell proteins for a balanced orchestration (regulation) of skin inflammation, skin regeneration and skin repair.

The said proteins obtained after said induced cell lysis comprise a mixture of one or more proteins and may or may not contain other skin cell constituents such as lipids, polysaccharides and nucleic acids and/or other bio-molecules.

Said induced cell lysis allows obtaining said proteins as a physiological, natural or normal (or naturally balanced) mixture of proteins present in the cell at the moment of induced cell lysis. In contrast to obtaining said proteins by induced cell lysis, the incorporation of viable cells into a composition for the treatment of skin conditions, disorders or diseases does not allow obtaining said proteins. The proteins obtained when viable cells are incorporated into a composition are of different characteristics and properties than the proteins obtained by induced cell lysis.

Said fetal skin cell proteins comprise cytokines including growth factors, interleukins, lymphokines, monokines, interferons, colony stimulating factors and chemokines. In addition, said fatal skin cell proteins comprise also other proteins or peptides such as enzymes, structural proteins of the extracellular matrix such as collagen, elastin, fibronectin, fibrillin and/or laminin. The said structural proteins can be present in the form of proteoglycans; where the protein is attached to chains of repeating disaccharide units termed of glycosaminoglycans (GAGs).

In addition, the said fetal skin cell proteins also comprise other proteins or peptides including but not limited to neuropeptides, neuropeptide antagonists, proteases, and/or protease inhibitors.

The fetal skin cell proteins can be easily manipulated, purified, separated, concentrated, modified, fractionated, stabilized and stored. Furthermore, the fetal skin cell proteins can be integrated into differing delivery forms, carriers and formulations with or without previously mentioned modifications.

Fetal skin cells used for the preparation of fetal skin cell proteins can be obtained from whole skin tissue, fractions of skin tissue or skin biopsies and/or skin cells obtained from a fetal skin cell culture. Fetal skin cell cultures or fetal skin cell lines are obtained from whole skin tissue, fractions of skin tissue or skin biopsies using standards skin culture procedures and techniques. The fetal skin cells or fetal skin cell lines are primary cells (cell lines with a limited life span).

In order to obtain continuous or immortalized fetal skin cells or fetal skin cell lines, fetal skin cells can be immortalized. Continuous or immortalized cells are highly desirable because they provide a stable, potentially infinite supply of cells having defined characteristics. In contrast, non-immortalized cells are only capable of growing for a finite number of cell divisions in vitro. In addition, primary cells are of greater variability than immortalized cells making it difficult to obtain cells and cell substrates with reproducible characteristics. The downside of using immortalized cells is that immortalized cell lines may be of a malignant phenotype. However, recent advances in our ability to engineer immortalized cell lines using well-defined immortalization techniques allow producing continuous or immortalized cell lines with little probability to be of malignant phenotype. Major advances in cell immortalization technology have been developed over the past few years. Normal mammalian or somatic cells have a finite life span due in part to their inability to maintain telomere length and chromosome stability. Telomerase expression has been used, either alone or in the company of other immortalizing genes, to create genetically stable, non-tumorigenic cell lines capable of apparently indefinite proliferation.

Fetal skin (fetal skin tissue) are taken from a human fetus or an animal fetus. Generally, human fetal skin tissue is taken at any age of gestation. However, fetal tissue is best taken during the gestation period of scarless wound healing before mid-gestation to the early third trimester. For instance, human fetal skin tissue is preferentially taken between 6 to 24 weeks of gestation. More preferentially, the fetal skin tissue is taken between 8-18 weeks of gestational age. Most preferentially, human skin tissue is taken from a human fetus between 12-16 weeks of gestation.

Fetal skin biopsies can be obtained following pregnancy interruption, after surgery in utero or by endoscopy or other means in relation to prenatal diagnostics as described by Holbrook K. A. et al. (Arch Dermatol. 1993, 129: 1437-1454) or Cadrin C. and Golbus M. S. (West J Med. 1993, 159: 269-272).

Women making a tissue donation following pregnancy interruption, surgery in utero or prenatal diagnostics will be serologically screened for a variety of infectious diseases, including but not limited to human immunodeficiency virus, hepatitis B virus, hepatitis C virus, cytomegalovirus and syphilis Donor eligibility and donor (mother) serology should be assessed according to the current FDA (http://www.fda.gov/cber/index.html) and ICH (http://www.ich.org) regulations, guidelines and recommendations at the moment of tissue collection.

When fetal skin tissue is obtained following a pregnancy interruption for medical and/or other reasons, a piece of fetal skin tissue of sufficient large size to prepare a cell culture can be obtained by fetal skin biopsy and/or surgical excision from the aborted fetus. The tissue collection is performed according to legal and ethical rules, where the pregnancy interruption is performed. Fetal skin tissue obtained after pregnancy interruption is used for establishing a fetal skin cell bank and/or fetal skin cell line.

Surgical intervention is currently performed on highly selected fetuses with anatomical deformities that have a high mortality or severe morbidity when treated postnatally. In the future, in utero surgical intervention for non-life-threatening disease may become possible as fetal surgery becomes safer for the mother and fetus. Fetal skin tissue obtained after surgery in utero can be used for establishing a fetal skin cell bank and/or fetal skin cell line.

In order to diagnose diverse forms of severe genodermatoses (J Dermatol Sci 1999, 19: 1-8) such as bullous diseases (e.g. epidermolysis bullosa), keratinization diseases (e.g. harlequin ichthyosis), pigment cell disorders (e.g. oculocutaneous albinism), and disorders of the epidermal appendages (e.g. ectodermal dysplasias), as well as to perform prenatal confirmation of true fetal trisomy 22 mosaicism of the fetus, samples of fetal skin are obtained by biopsy or other means.

Generally, prenatal diagnostic is performed between 16 to 22 weeks' gestation depending on the diagnostic. Skin samples not used for diagnostics; in case the fetus is not affected by the disease, can be used for establishing a fetal skin cell bank and/or fetal skin cell line.

The fetal skin tissue is fragmented into small to medium sized pieces (e.g. 0.5 mm$^3$) by scalpel, knife and/or any other cutting devices and then placed into appropriate culture plates (e.g. plates of 10 cm diameter) at a given seeding density (e.g. 10 pieces per 10 cm plate).

Fetal skin cells are obtained by outgrowing from fetal skin tissue fragments placed into culture plates under appropriate cell culture conditions. Suitable cell culture conditions include, but are not limited to the use of Delbecco's Modified Eagles Medium (DMEM) supplemented with 10% fetal calf serum (FCS) alone. Cell growth is obtained under standard cell culture condition in a cell culture incubator (e.g. at 37° C. in a humidified atmosphere of >80% relative humidity air and 5 to 10% $CO_2$).

After an appropriate culture time, generally between 5 to 12 days depending on the exact cell culture conditions and the fetal skin tissue selected, culture plates containing remaining fetal skin tissue and outgrown fetal skin cells can be separated in order to harvest individual fetal skin cells originating from the fetal skin tissue. Enzymes such as trypsin (e.g. 0.25% trypsin in 0.1% ethylene-diamine-tetraacetic acid (EDTA)) or other proteolytic enzymes (e.g. proteases) are preferentially used for this purpose. At this point, fetal skin cells obtained from fetal skin tissue placed in culture plates can be collected, harvested and optionally stored before further manipulation or use. Cells can be collected after centrifugation (e.g. 2000 g for 15 min) or other means of cell collection.

Optionally, the fetal skin cells can be immortalized. The production of immortalized cell lines derived from cell tissues including fetal skin keratinocytes has been previously described (Burnett T S et al, J Gen Virol 64, 1983, 1509-1520; Brown K W et al, Br J Cancer 56, 1987, 545-554). In general such methods comprise transfection or transformation of cells.

Immortalization refers to the production of cells, which are able to be cultured for prolonged time periods in vitro, ideally indefinitely. An immortal cell is immortal under defined growth conditions. A cell is considered immortal if it can be cultured under the defined growth conditions for more than 20 passages, preferably more than 30 passages, still more preferably more than 40 passages, and yet more preferably for more than 50 passages. These cells are also referred to as continuous cell lines. By contrast non-immortalized cells are only capable of growing for a finite number of cell divisions in vitro. Immortalized cells are highly desirable because they provide a stable, potentially infinite supply of cells having defined characteristics. In this application, the terms "conditionally immortal" and "immortal" are used interchangeably.

Techniques for producing immortalized fetal cell lines include irradiation, chemical carcinogens, viruses, recombinant viruses and recombinant DNA (Stacey G. and MacDonald C., Cell Biol Toxicol 17, 2001, 231-246). Techniques to create genetically stable and non-tumorigenic cell lines are preferentially used for immortalization of fetal skin cells. For instance, such an immortalization technique consists in the transfection of the catalytic subunit of telomerase (hTERT) gene into normal primary cells (Bodnar A. G. et al., Science 279, 1998, 349-352; Morales C. P. et al., Nature Genetics 21, 1999, 115-118). This approach has been successfully applied to human skin fibroblasts (Vaziri H. F. and Bechimol S., Oncogene 18, 1999, 7676-7680) and other cell types. This transfection technique allows obtaining cell lines of extended life-span, which unlike those often produced by oncogene transfection, are stable and retain key characteristics of primary cells. Otherwise, the immortalizing gene, SV40 T antigen, is now being applied in new combinations, in collaboration with telomerase, and in Cre-lox constructs which allow reversible immortalization (Cascio S. M., Artificial Organs 25, 2001, 529-538).

One of the most common methods of producing immortalized human cell lines involves the use of SV40 sequences and more specifically the SV40 large T antigen DNA as an immortalizing agent. Alternatively, the cells may be transfected by electroporation, or other well known techniques as described in Sambrook et al., Molecular Cloning, A Laboratory Manual, Cold Spring Harbor Press, 1988, incorporated herein by reference.

Several scientific publications report on the use of SV40 vectors and SV40 large T antigen sequence containing vectors to produce immortalized cell lines. The introduction of such sequences is generally effected by infection using SV40 virus or with a hybrid adenovirus-12 SV40 hybrid virus or by transfection of cells with a recombinant plasmid containing the Rous sarcoma virus long terminal repeat and the Ori-SV40 early region by strontium phosphate co-precipitation.

Another known method for producing immortalized cell lines, and immortalized keratinocytes in particular, involves transfection or infection of cells with human papilloma virus (HPV) DNA sequences.

Further methods are the use of at least one gene or polypeptide selected from the group consisting of the 12S and 13S products of the adenovirus E1A genes, hTERT, SV40 small T antigen, SV40 large T antigen, papilloma viruses E6 and E7, the Epstein-Barr Virus (EBV), Epstein-Barr nuclear antigen-2 (EBNA2), human T-cell leukemia virus-1 (HTLV-1), HTLV-1 tax, Herpesvirus saimiri (HVS), mutant p53, myc, c-jun, c-ras, c-Ha-ras, h-ras, v-src, c-fgr, myb, c-myc, n-myc, and Mdm2.

The use of serum-free medium (or media) during the isolation and production of immortalized epithelial cells, and specifically human keratinocytes has been described. For example, Barbosa et al. (Oncogene, 4, 1989, 1529-1532) describe initially culturing human keratinocytes transfected by electroporation or lipofection in low calcium, serum-free medium until confluence.

The fetal cells may naturally secrete the one or more biologically active molecules. Alternatively, the cells may be genetically engineered to secrete an exogenous level of the one or more biologically active molecules. Secretion may be controlled by gene switching or it may be constitutive. For example, the cells can be engineered to express or enhance expression of a protein or other gene product, or to suppress a protein or gene product. Other manipulations can include the knockin (insertion, substitution) or knockout (ablation) of a gene or mutation of an existing gene or gene product.

Optionally, the cells can be mitotically inactivated before use. For example, this mitotic inactivation can be accomplished by irradiation including gamma or X-Rays irradiation, and/or UV light. The inactivation can be also accomplished the administration of chemically-based mitotic inhibitors and/or through incubation with mitomycin.

One advantage of the innovation is the creation of a fetal skin cell bank or fetal skin cell bank system, which enables sustained and immediate supply of fetal skin cell proteins. A cell bank system is a system whereby successive batches of a product are manufactured by cell culture using cells derived from the same master cell bank (MCB). A number of containers from the master cell bank are used to prepare a working cell bank (WCB). Generally, the cell bank system is validated for a passage level or number of population doublings beyond that achieved during routine production.

The master cell bank is a culture of cells distributed into containers in a single operation, processed together in such a manner as to ensure uniformity and stored in such a manner as to ensure stability. A master cell bank is usually stored at $-70°$ C. or lower. The master cell bank is generally well characterized. The working cell bank is a culture of cells derived from the master cell bank and intended for use in the preparation of production cell cultures. The working cell bank is usually stored at $-70°$ C. or lower.

For example, a fetal skin cell bank is obtained or created by harvesting fetal skin tissue from donor fetal skin; growing the fetal skin tissue and proliferating fetal skin cells under appropriate cell culture conditions; separating by enzymes such as trypsin, collagenase and/or other proteases the tissue and cells of the resulting cultures to allow their suspension; pooling the suspended fetal skin cells to make a generally uniform suspension of cells from the culture; gently mixing with a cryoprotectant (see below); sealing aliquots of the fetal skin cell suspension in ampoules; and freezing the aliquots (see below), thereby preparing a fetal skin cell bank.

Preferably, the fetal skin cells are fetal dermal fibroblasts and/or fetal epidermal keratinocytes, and/or fetal melanocytes or any possible combination or mixture thereof.

Various approaches to cryopreservation of cells including tissues as well as proteins can be used. In freeze-thaw techniques, the extracellular solution is frozen, whereas steps are taken to minimize intracellular ice formation. In vitrification procedures, there is an attempt to prevent ice formation throughout the entire sample. The former approach is problematic in that if ice crystals are formed inside the cells, they are detrimental to cell viability upon thawing. However, cells could survive a freeze-thaw cycle if they are cooled at controlled rates in the presence of non-toxic levels of cryoprotectants. The latter approach of vitrification seeks to avoid potentially damaging affects of intra- and extracellular ice by depressing ice formation using very high concentrations of solutes and/or polymers. However, the cell damage may occur to long exposure to toxic levels of these additives required for vitrification.

Cryoprotectant solutions containing glycerol, propylene glycol, ethylene glycol, and/or dimethylsulfoxide are preferred. In one preferred embodiments of this invention, the cryoprotectant solution contains 1.5 M to 2.5 M glycerol, preferably 2 M glycerol, in a base of Dulbecco's Modified Eagle's Medium (DMEM). These solutions can be modified and optimized by one of skill in the art using known cryoprotectants and freezing, storing, thawing, and rinsing procedures that are compatible with maintaining maximal viability, depending on the particular application.

The cooling step is one of the most critical steps in a freeze-thaw protocol. Given that each cell type may have drastically different characteristics, the optimal cryopreservation conditions can vary by orders of magnitude for different cell types. In one of the preferred embodiments of this innovation, the freezing of the cells in appropriate aliquots is achieved by lowering the temperature by $1°$ C. per min until a temperature of lower than minus $70°$ C. is reached. Approximately 24 hours later the cells are transferred into liquid nitrogen and/or the vapor phase of liquid nitrogen for storage (for 10 years or more) until use.

Proteins and other cell-related material or biomolecules are obtained by induced cell lysis or induced cell disruption (Becker et al.: Biotech Advs 1, 1983, 247-261; Schutte et al.: Biotechnol Appl Biochem 12, 1990, 599-620). Although some biological proteins are secreted from the cell or released during autolysis (spontaneous or natural cell lysis), the preparation of many other proteins requires induced cell lysis to obtain (release) proteins within the cell (intercellular proteins).

Wide ranges of techniques exist or are under development in trying to disrupt the cells. These techniques can be grouped into two categories '"mechanical" and "non-mechanical'. They can be employed either alone or in combination to disrupt cells. Mechanical cell disruption is achieved by the use of homogenizers, bead mills, jet stream and constant cell disruption systems. Non-mechanical cell disruption is obtained by physical, chemical or enzymatic means. Physical means are decompression, osmotic shock, thermolysis or sonnication. The use of antibiotics, chelating agents, detergents, high pH, chaotropens or solvents are chemical means. The use of lytic enzymes, lysis or autolysis are enzymatic means.

Milling, high pressure homogenization (e.g. French press, X-press, etc), ultrasonication and freeze-thawing use of shear and pressure to disrupt cells. Thereby, care has to be taken to avoid or limit the loss of enzymatic activity under conditions that are used to achieve cell breakage.

In one of the preferred embodiments, the fetal skin cells are lysed (disrupted) by one or multiple cycles of freeze-thawing. For that purpose, the fetal skin cells are suspended in an aqueous system before freeze-thawing. The aqueous systems include but are not limited to culture medias (e.g. DMEM, MEM, etc.), aqueous buffer systems (e.g. pH 7.4 buffer, etc.), physiological buffers (e.g. PBS, PBS w/o $Ca^{++}$ and $Mg^{++}$, HEPES, etc.), non-physiological buffer systems, aqueous solvents (e.g. water, etc.) and/or mixtures and combinations thereof. In a preferred embodiment of this invention, the cells are suspended in phosphate buffered saline (PBS) with or without $Ca^{(II)}$ and $Mg^{(II)}$ (called phosphate buffer saline system).

The fetal skin cell proteins are obtained after freeze-thawing of a fetal skin cell suspension (dispersion) obtained by suspending fetal skin cells in the aqueous system at a specific cell concentration. The cell concentration of the fetal skin cell suspension may vary between a few thousand to several billion cells per milliliter (ml) aqueous system. In one of the preferred embodiment of the invention, the fetal skin cell suspension contains between 100 to 60,000,000 fetal skin cells per milliliter aqueous system. In another embodiment, the fetal skin cell suspension contains between 1,000,000 to 30,000,000 fetal skin cells per ml aqueous system. In another embodiment, the fetal skin cell suspension contains between 5,000,000 to 25,000,000 fetal skin cells per ml aqueous system. In a preferred embodiment the fetal skin cell suspension contains between 10,000,000 to 20,000,000 fetal skin cells per ml aqueous system.

The fetal skin cell proteins are prepared with viable fetal skin cells, with non-viable fetal skin cells or with a mixture of viable and non-viable fetal skin cells. In the preferred embodiment of this invention, fetal skin cells with a viability of greater than 80% are suspended in the aqueous system and subsequently lysed by freeze-thawing.

In another embodiment, fetal skin cells with a viability of equal or lower than 80% are suspended in the aqueous system and subsequently lysed by freeze-thawing. Generally, cell lysis is performed immediately after preparation of the fetal skin cell dispersion in the aqueous system. Cell viability can be measured using classical cell viability assays.

Optionally, the aqueous system used for freeze-thawing can be supplemented before cell lysis with cryoprotectants, protease inhibitors, glycosidase inhibitors, chemicals stabilizing proteins, chemicals preventing protein denaturation, antioxidants, preservatives, antimicrobials and/or other chemicals. The supplementation may help to preserve and/or stabilize fetal skin cell proteins obtained after induced cell lysis of fetal skin cells. Otherwise, the supplementation may help maintaining or enhancing the potency or the activity of the fetal skin cell proteins.

The fetal skin cell proteins can be optionally purified in order to obtain fetal skin cell proteins of a desired composition and/or purity. For this purpose, well known techniques as described in 'Protein Analysis and Purification—Benchtop Techniques' (Rosenberg I. M., Birkauser, Boston), incorporated herein by reference, can be used.

Optionally, the fetal skin cell proteins can be separated into a pellet (containing mostly not soluble material) and a supernatant (containing mostly soluble material) after centrifugation. The supernatant can be integrated into a carrier with or without further manipulation and/or purification. It contains fetal skin cell proteins. Alternatively, the cell pellet can be integrated into a carrier with or without further manipulation and/or purification.

Optionally, the fetal skin cell proteins or any fraction thereof can be chemically modified by acetylation, esterification, pegylation, glycosylation and/or can be chemically cross-linked to a polymer in order to improve chemical/physical stability and therapeutic activity of the fetal skin cell proteins.

A variety of articles known to those skilled in the art describe protein stabilization and a wide variety of compounds are used to cryopreserve (Cryobiology 25, 1988, 244-255; Pharm Res 8, 1991, 285-291; Advanced Drug Delivery Reviews 46, 2001, 307-326). The more common cryoprotectants include, e.g., sugars, polyols, certain amino acids and synthetic polymers. Other cryoprotectants include, e.g., inorganic salts, organic salts or miscellaneous ingredients. Non limiting examples of suitable sugars include, e.g., sucrose, lactose, glucose, trealsose and maltose. Examples of polyols used include, e.g., ethylene glycol, glycerol, sorbitol, mannitol, inositol, xylitol, 2-methyl-2,4-pentanediol. Examples of amino acids used include, e.g., sodium glutamate, proline, alanine, glycine, lysine and hydroxyproline. Examples of polymers used include, e.g., polyethylene glycol, dextran and polyvinylpyrrolidone. Examples of inorganic salts used include, e.g., sodium sulfate, ammonium sulfate, potassium phosphate, magnesium sulfate and sodium fluoride. Examples of organic salts include, e.g., sodium acetate, sodium polyethylene, sodium caprilate, propionate, lactate and succinate. Examples of miscellaneous cryoprotectants include, e.g., dimethylsulfoxide, ethanol, trimethylamine N-oxide, sarcosine, bataine, γ-aminobutyric acid, octopine, alanopine and strombine.

Protease inhibitors can be further used to prevent proteolytic hydrolysis of fetal skin cell proteins. Protease inhibitor include but are not limited to serine protease inhibitors (e.g. leupeptin, antipain, PMSF, AEBSF, etc.), cystine protease inhibitors (e.g. leupeptin, chymostatin, etc.), aspartic protease inhibitors (e.g. pepstatin A, etc.), metalloproteinase inhibitors (e.g. EDTA, 1,10-phenanthroline, bestatin, phosphoramidon, TIMP 1, TIMP 2, etc.) and combinations thereof.

Protease inhibitors are added to the aqueous system before performing the induced cell lysis and/or to the fetal skin cell proteins obtained after performing the induced cell lysis. In one of the preferred embodiments, EDTA is added to the aqueous system used for freeze-thawing.

Proteins can be preserved also by other means such as freeze-drying or lyophilization.

Otherwise, agents to stabilize fetal skin cell proteins can be added to the composition comprising fetal skin cell proteins.

Cell culture medium supplies the components for cell growth in a controlled, artificial environment in vitro. Once the culture medium is incubated with cells, it is known as "spent" or "conditioned medium". Conditioned medium contains many of the original components of the medium, as well as a variety of cellular metabolites and secreted proteins, including, for example, biologically active growth factors, inflammatory mediators and other extra-cellular proteins. In one of the embodiments of this invention, conditioned medium obtained after culturing fetal skin cells in a cell culture medium may be used and incorporated into a carrier for topical application.

Composition Preparation

The fetal skin cell proteins can be incorporated into a carrier suitable for topical, mucosal, ocular, rectal and/or vaginal application.

Acceptable carriers include carriers suitable for topical, mucosal, ocular, rectal and/or vaginal application are those which are applied locally; typically directly to the skin and mucous membranes as well as to compromised, not intact or pathologic and/or wounded skin and mucous membranes. This is in contrast to typical systemic preparations, which may be taken orally or by injection, and work through the system rather than directly on the body's surface.

Preferably, the carrier is a topically acceptable carrier. The term "topically acceptable carrier" refers to any vehicle, adjuvant, excipient, diluent, which is known in the pharmaceutical, food or cosmetic arts for application onto the skin (or the epithelial layer of the mucosal tissue) and is approved for dermal/mucosal administration. The choice of carrier will be determined by the particular active agent, for example, its dissolution in that specific carrier (hydrophilic/hydrophobic), as well as by other criteria such as the size and the nature of the area to which it should be applied (for example in the scalp shampoos may be used while for small area a salve is more applicable, etc.).

These may include topically acceptable liquids, creams, oils, lotions, ointments, gels, or solids, including but not limited to conventional cosmetic night creams, cosmetic day creams, foundation creams, suntan lotions, sunscreens, hand lotions, hydrogels, make-up and make-up bases, masks, sponges and the like. The compositions can contain other optional suitable ingredients such as estrogen, vitamin A, C and E, alpha-hydroxy of alpha-keto acids such as pyruvic, lactic or glycolic acids, lanolin, vaseline, aloe vera, methyl or propyl paraben, pigments and the like. Suitable topically acceptable carriers include water, petroleum jelly (vaseline), petrolatum, mineral oil, vegetable oil, animal oil, organic and inorganic waxes, such as microcrystalline, paraffin and ozocerite wax, natural polymers, such as xanthanes, gelatin, cellulose, collagen, starch, or gum arabic, synthetic polymers, such as discussed below, alcohols, polyols, and the like. Excipients include solvents, surfactants, emollients, preservatives, colorants, fragrances and the like. Preferably, the carrier is a water miscible carrier composition that is substantially miscible in water. Such water miscible topical cosmetically acceptable carrier composition can include those made with one or more appropriate ingredients set forth above but can also include sustained or delayed release carrier, including water containing, water dispersable or water soluble compositions, such as liposomes, microsponges, microspheres or microcapsules, aqueous base ointments, water-in-oil or oil-in-water emulsions, gels or the like.

The fetal skin cell proteins can be incorporated into the composition between 0.001% to 95% by volume or weight. The fetal skin cell proteins are preferentially incorporated between 0.01 and 5% by volume or weight.

In one of the preferred embodiments, the fetal skin cell proteins are prepared with a suspension (dispersion) containing between 10 million to 20 millions cells per ml physiological buffer (e.g. PBS), and the so obtained fetal skin cell proteins are incorporated into a carrier for topical, mucosal, ocular, rectal and/or vaginal applications between 0.05% to 0.25% by volume or weight.

In various embodiments, the carrier is a topical preparation or dosage form. Topical preparations are ointments, creams, gels and lotions. The definition of these topical dosage forms is given by Bhuse L. et al. (Int J Pharm 295: 2005, 101-112).

In another embodiment, the carrier is a liquid, a foam, a mousse, a spray, an aerosol, an oil-in-water emulsion, a water-in-oil emulsion, a triple emulsion, a nanoemulsion, a microemulsion, a hydrogel, a solution, a paste, a jelly and/or a dispersion or suspension. The carrier may contain niosomes, liposomes, nanospheres, microspheres, nanoparticules, microparticules, lipid droplets, solid particles, pigments and/or water droplets.

In one of the preferred embodiments, the carrier is a cream. The cream may be either an oil-in-water based carrier, or a water-in-oil based carrier. In another preferred embodiment, the carrier is a gel and/or a hydrogel.

Those skilled in the art will recognize that any reference to a composition of the invention includes any composition containing one or more fetal skin cell proteins in conjunction with a carrier.

The compositions of the invention may optionally contain structural extracellular matrix proteins, collagen, alginate, alginate beads, agarose, chitosan, fibrin, fibrin glue, fibrinogen, blood plasma fibrin beads, hyaluronic acid, sodium hyaluronate, whole plasma or components thereof, laminins, fibronectins, proteoglycans, heat shock proteins, chitosan, heparin, and/or other synthetic polymer or polymer scaffolds and/or solid support materials.

Those skilled in the art will recognize that additional active agents can be added in the methods and compositions of the invention. These agents may include, e.g., anti-inflammatory agents, anti-septic agents, antioxidants, anti-acne agents, astringents, anorectal agent, analgesics, anestetics, antipruritics, counter irritants, antimicrobial agents, antibiotics, antihistamine agent, anti-psoriasis agents, anti-rosacea agents, anti-scar agents, dandruff agent, hair growth agents, anti-hair loss agent, antifungal agents, antibiotics, vitamins, wound healing agents, keratolytic agents, antioxidants, hormones, stimulants, skin bleaching agents, skin protectant agents, skin coloring agents, wart removers, sunscreens and any appropriate combinations thereof. Cosmetic ingredients may be further added.

Analgesics include amine and caine-type local anesthesics, alcohol and ketones anesthesics, antihistamines, hydrocortisones and/or appropriate combinations thereof.

Amine and caine-type local anesthesics include over-the-counter (OTC) external analgesic drugs including benzocaine, butamben picrate, dibuccaine, diemethisoquin, dyclonine, lidocaine, pramoxine, tetracaine, their respective salts and appropriate combinations thereof. In a preferred embodiment, pramoxine hydrochloride is selected as analgesic. The preferred embodiment contains 0.5 to 1% pramoxine hydrochloride.

Alcohol and ketones type local anesthesics include OTC external analgesic drugs including benzyl alcohol, camphor, menthol, phenol, resorcinol and appropriate combinations thereof. In some preferred embodiments, camphor or menthol are selected as analgesics.

Antihistamines type local anesthesics include OTC external analgesic drugs including diphenhydramine, tripelennamine, their respective salts and appropriate combinations thereof.

Hydrocortisone type local anesthesics include OTC external analgesic drugs including hydrocortisone and hydrocortisone acetate.

Counter irritant type OTC analgesics include allyl isothiocyanate, diluted ammonia solution, methyl salicylate, turpentine oil, camphor, menthol, histamine dihydrochloride, methyl nicotinate, capsaicin, *capsicum, capsicum* oleoresin and appropriate combinations thereof.

Skin protectant OTC drugs include allantoin, aluminium hydroxide, calamine, coca butter, cod liver oil, colloidal oatmeal, dimethicone, glycerin, hard fat, kaolin, lanolin, mineral oil, petrolatum, topical starch, white petrolatum, zinc acetate, zinc carbonate, zinc oxide, aluminium acetate, aluminium sulfate and appropriate combinations thereof.

Antimicrobial OTC drugs include alcohol, benzalkonium chloride, benzethonium chloride, camphorated metacresol, camphorated phenol, eucalyptol, hexylresorcinol, isopropyl alcohol, menthol, methylbenzethonium chloride, methyl salicylate, phenol, povidone-iodine, thymol, bacitracin, bacitracin zinc, chlortetracycline hydrochloride, neomycin sulfate, tetracycline hydrochloride, clioquinol, haloprogin, miconazole nitrate, tolnaftate, undecylenic acid and its calcium, copper and zinc-salts, clotrimazole, resorcinol, resorcinol monoacetate, salicylic acid, sulfur, benzoyl peroxide and appropriate combinations thereof.

Ideally, agents, ingredients and/or actives will be chosen that do not or only minimally interfere with the activity of fetal skin cell proteins.

Concentration or concentration ranges of above OTC drugs are known to those skilled in the art. Moreover, various combinations of these OTC drugs may also be possible.

Information regarding the preparation of pharmaceutical compositions, can be found, e.g., in Volume 3: Liquid Products, Volume 4: Semisolid Products and Volume 5: Over-the-Counter Products, of the 'Handbook of Pharmaceutical Manufacturing Formulations' (edited by S. K. Niazi, CRC Press, Boca Raton, 2004). Moreover, information regarding the preparation of cosmetic or cosmeceutical compositions may be found in the formulary archive of the Happy Magazine (http://www.happi.com/special/formula1.htm). In addition, formulary information for cosmetic or cosmeceutical compositions can be also obtained from diverse ingredient suppliers such as Croda, Ciba, BASF, Dow Chemicals, etc.

Composition Uses

The invention also provides methods for preventing or treating a skin condition, disorder or disease by administering a therapeutically effective amount of the composition of the invention to the susceptible or affected area of the subject's skin.

The skin condition, disorder or disease to be treated or prevented include, but are not limited to inflammatory skin conditions, neurogenic or neuroinflammatory skin conditions, acute and chronic wounds, acute and chronic ulcers, and burns.

In one of the preferred embodiments, the inflammatory, neurogenic and/or neuroinflammatory skin conditions is vulvodynia comprising vulvar vestibulitis and vulvar lichen sclerosus.

In another embodiment of this invention, said skin conditions disorders or diseases treated by the said compositions include mucosal conditions, disorders or diseases where mucosa or mucosal tissue is adjacent to the treated skin.

Examples of skin conditions, disorders, or diseases treated by the compositions of the invention further include acne, atopic dermatitis, allergic contact dermatitis, atrophie blanche, dandruff, dermatitis, hand eczema, herpetiformis, diaper rash, eczema, generalized exfoliative dermatitis, keloids, localized or generalized pruritus, photo-dermatoses, peri-ulcers, psoriasis, scars, sebaceous cyst, seborrheic dermatitis, rosacea, and/or xerosis.

Examples of skin conditions, disorders or diseases treated by the compositions of the invention also include wounds; including acute and chronic wounds, ulcers; including acute and chronic ulcers, and/or burns.

Examples of skin conditions, disorders, or diseases treated by the compositions of the invention further include wounds, ulcers, and/or burns during and/or after single or repetitive treatment with a skin graft (allograft, autograft), three-dimensional skin construct, and/or other wound care regimens.

Wounds after surgery are also treated by the compositions of the invention. Surgery includes, but is not limited to non-cosmetic, cosmetic, plastic and/or reconstructive surgery procedures.

Cosmetic, plastic and reconstructive surgery procedures include, but are not limited to breast lift, breast augmentation or reduction, facelift, forehead lift, surgery of the nose, surgery of the ear, surgery of the eye lid, surgery of the abdomen, liposculpturing, liposuction, scar revision, fat transfer, soft-tissue augmentation, cryosurgery or cryotherapy, hair transplantation, nail surgery, sclerotherapy, laser surgery, tattoo removal and/or vein surgery.

In addition, skin conditions, disorders or diseases treated by the said compositions comprise non-pathologic skin conditions including, but not limited to, normal skin and/or healthy skin, intrinsically and/or extrinsically aged or photo-aged skin. Furthermore, skin conditions, disorders or diseases treated by the said compositions comprise skin exposed (in contact with) to cosmetic products, pharmaceutical or dermatological products, household products, industrial products and/or products containing ingredients harmful for skin such as corrosive chemicals, skin irritants and skin allergens.

Cosmetic and/or dermatological products include, but are not limited to products containing one or more exfoliant, keratolytic, wart remover, hair remover, chemical peel, physical peel, self-tanning ingredient, fragrance, deodorant, anti-dandruff active, anti-acne active, anti-inflammatory agent, anti-rosacea active, anti-psoriasis active, make-up cosmetic, dye, color additive, pigment, skin lightener, skin whitening agent, antioxidant, lipid, skin nutrient, sunscreen, surfactant, polymer, protein, myorelaxant, anti-aging ingredient, anti-wrinkle agent, moisturizer, humectant, vitamin, emollient, film-forming agent, liposome, nanoparticle, microparticle, nanosphere, microsphere and/or any possible mixtures and combinations thereof.

In another group of preferred embodiments of this invention, the said compositions are used to treat skin and/or skin conditions occurring from cosmetic and/or dermatological procedures. Cosmetic and/or dermatological procedures include, but are not limited to light chemical peels, medium chemical peels, deep chemical peels, physical peels, waxing, microdermabrasion, dermabrasion, light treatments (intense pulse light, photomodulation, treatments with visible, non-visible, infrared and/or ultraviolet light), laser treatments, radiofrequency treatments, thermal treatments (heat, cold, cycles of heat and cold), electrical treatments, sonnication treatments, mechanical treatments (massage, pressure, suction, vibration, friction, abrasion), oxygen and/or ozone treatments, injections and/or any combinations thereof. The said compositions are used in combination with said cosmetic and/or dermatological procedures; either before, after and/or during (in parallel) the cosmetic and/or dermatological procedures.

The subject may be selected from the group consisting of humans, non-human primates, wildlife, dogs, cats, horses, cows, pigs, sheep, rabbits, rats and mice. In one preferred embodiment, the subject is a human or an animal, such as a horse, a dog or a cat.

The invention is further defined by reference to the following examples. It is understood that the foregoing detailed description and the following examples are illustrative only and are not to be taken as limitations upon the scope of the invention. It will be apparent to those skilled in the art that many modifications, both to the materials and methods, may be practiced without departing from the purpose and interest of the invention. Unless otherwise defined, all technical and scientific terms used herein have the same meaning as commonly understood by one of ordinary skill in the art to which this invention belongs. All publications, patent applications, patents, and other references mentioned herein are incorporated herein by reference in their entirety. In the case of conflict, the present specification, including definitions, will control.

EXAMPLES

Example 1

Fetal Skin Tissue Sampling

A fetal skin tissue sample (skin biopsy) was obtained from fetal skin immediately following pregnancy interruption in accordance with the policies and procedures of the Ethics Committee of the University Hospital Lausanne, Switzerland.

Donor eligibility and donor (mother) serology was assessed according to current FDA (http://www.fda.gov/cber/index.html) and ICH (http://www.ich.org) regulations, guidelines and recommendations. The donor's medical history and serology was compatible with those guidelines and recommendations at the period of tissue donation.

Donor eligibility included the assessment of clinical evidence for HIV, Hepatitis B, Hepatitis C, human TSE including CJD, *Treponema pallidum*, and risks associated with xenotransplantation (not receiving corneal and/or dura mater grafts and not receiving human growth hormones obtained from cadavers) by interview. Serology testing included assessment for presence of HIV I, HIV II, Cytomegalovirus, Hepatitis A, Hepatitis B, Hepatitis C, Rubella, Toxoplasmosis, *Treponema pallidum* (syphilis) using validated antibody assays. The donor medical history did not reveal any evidence for presence of viruses. This was confirmed by serology testing at time of biopsy and after 3 months.

In general, fetal skin tissue or skin biopsy was taken before scarless wound healing or repair occurs; e.g. before mid-gestation to the early third trimester. In humans, human donor tissue or skin biopsy was of 12-16 weeks gestation. However, biopsies from human donors were also obtained at an earlier and a later age of gestation (including between 6-11 and 17-24 weeks). Generally, the biopsy was of full skin-thickness. Alternatively, a partial thickness biopsy was performed; it contained dermal and/or epidermal fetal skin tissue. At earlier age of gestation, the biopsy contained predominately dermal fetal skin tissue. In order to prepare a fetal skin cell bank and/or fetal skin cell line, a piece (or sample) of fetal skin tissue of a sufficient large size to prepare a cell culture was obtained by fetal skin biopsy and/or surgical excision. Generally, the fetal tissue sample was between 0.5 cm² to 8 cm².

Fetal skin tissue (or fetal skin biopsy) was also obtained from a horse. Similar methods and procedures were used to obtain equine fetal skin cell proteins as described in the following examples.

The skilled artisan will understand that there are other possibilities to obtain fetal skin tissue samples for establishing a fetal skin cell bank. Fetal skin tissue can be obtained are after surgery in utero and/or when performing prenatal diagnostics requiring fetal skin tissue sampling.

Example 2

Fetal Skin Cell Bank

A typical procedure for establishing a fetal skin cell bank comprising a Master (MCB) and a Working Cell Bank (WCB) starting with fetal skin tissue and/or a fetal skin biopsy sample is hereby given. Generally, a cell bank is created with fetal skin from one donor. The fetal skin sample to create the cell bank was obtained as described in Example 1 after pregnancy interruption. The fetal skin sample (biopsy) was obtained at 16 weeks gestation and was of approximately 4 cm².

From the skin sample, tissue fragments of about 0.5 mm³ and smaller were prepared by scissors and/or the use of scalpels or other cutting devices. The fragments were then seeded into sterile plates (e.g.: 10 cm diameter) at approximately 10 fragments per plate. These fragments were grown in Dulbecco's Modification of Eagle's Medium (DMEM) supplemented with 10% fetal bovine serum (FCS, Hyclone) in a 37° C., 10% $CO_2$ and 95% humidity incubator. Medium exchange occurred every second or third day. When cell growth approached confluence after approximately 1-2 weeks, the culture plates containing skin tissue and cells were trypsinized using 0.25% trypsin in 0.1% ethylene diamine tetraacetic acid (EDTA). The cells were transferred into a centrifugation tube and then centrifuged. Afterwards, the harvested cells (corresponding to cells at passage 0) were re-suspended in DMEM supplemented with 10% FCS and seeded in T175 Flasks (Nalge Nunc) at 2000 cells per cm². After reaching confluence, the cells (passage 1) were harvested as described before and then seeded in T175 Flasks at 3000 cells per cm² in order to obtain cells at passage 2. After harvesting cells at passage 2, they were aliquoted in appropriate cryovials (e.g. 1.8 ml) and then frozen in liquid nitrogen. For this purpose, cells were re-suspended in a freezing solution of DMEM, FCS and dimethyl sulfoxide (DMSO) at a ratio of 5:4:1 (all from Fluka) and frozen in 1 ml aliquots (containing between 4 to 8 million cells) at minus 70° C. or lower using a Cryo 1° C. Freezing Container (Nalge Nunc) to achieve a minus 1° C. per min cooling rate. After leaving the cells for 24 h in the Freezing Container, they were transferred to liquid nitrogen (or vapor phase) for storage. A MCB of fetal skin cells comprising several vials with frozen cells at passage 2 was obtained.

The human skin cell derived MCB was tested for endogenous and adventitious agents (sterility, mycoplasma and viruses) and identity in order to characterize the cell bank. This testing was conducted in accordance with the requirements of (current) Good Laboratory Practices (GLP) and with the (current) principles laid down by the European Medicines Agency (EMEA) and the Federal Drug Administration (FDA) guidelines including the International Conference of Harmonization (ICH) guidelines '*Viral safety evaluation of biotechnology products derived from cell lines of human or animal origin*' (Q5A) and '*Derivation and characterization of cell substrates used for production of biotechnological/biological products*' (Q5D).

Testing of the MCB did not detect mycoplasmas, bacteria or fungi. The MCB was shown by electron microscopy to contain no retroviral particles and no retroviral reverse transcriptase activity was detected. In addition, PCR based assays did not detect any human viruses, including human retroviruses. Other detection methods did not detect other viral adventitious agents in the MCB. The results of the tests conducted on the MCB were typical of a human cell line. The identity was confirmed to be human. In summary, the testing indicated that the MCB is free of viruses or viral adventitious agents, mycoplasmas, bacteria or fungi.

The WCB was established using a vial from the MCB, seeding the cells in appropriate culture flasks (e.g.: T175 Flasks from Nalge Nunc), harvesting at about confluence, aliquoting and then freezing the cells as described for the MCB. The WCB can be established at passage 3. Otherwise, the WCB can be established at passage 4 using a vial from the MCB after performing two passages. Cells of the WCB are stored in liquid nitrogen (or vapor phase) in cryovials of about 2 to 6 million cells per vial.

The human skin cell derived WCB was tested for adventitious agents (sterility and mycoplasma) and identity in order to characterize the cell bank. This testing was conducted in accordance with the requirements of (current) GLP and with the (current) principles laid down by the EMEA and the FDA guidelines including the ICH guideline '*Derivation and characterization of cell substrates used for production of biotechnological/biological products*' (Q5D).

Testing of the WCB did not detect mycoplasmas, bacteria or fungi. The results of the tests conducted on the WCB were typical of a human cell line. The identity was confirmed to be human. In summary, the testing indicated that the WCB is free of mycoplasmas, bacteria or fungi.

The person of skill in the art will understand that although the cell banking is described using a 4 cm$^2$ fetal skin sample at 16 weeks gestation obtained after pregnancy interruption as described in this example, other fetal skin tissue samples obtained at a different age of gestation and/or obtained after surgery in utero and/or obtained after prenatal diagnostics (as described in Example 1) may be used to establish a cell bank with appropriate modifications to the described conditions.

The skilled artisan will also understand that any number of methods of cell banking can lead to the creation of a fetal skin cell bank. As a simple alternative to the described method, the cell bank (MCB and/or WCB) may be established in a 37° C., 5% $CO_2$ and >80% humidity incubator. Alternatively, the cell bank can be established using differing culture containers (e.g. any number of roller bottles, multi-tray cell factories, cell bioreactors, etc.) and culture conditions (e.g. serum free, etc.) with appropriate modifications to the described conditions.

Example 3

Fetal Skin Cell Expansion

In order to produce fetal skin cell proteins, fetal skin cells from the fetal skin cell bank are used, seeded in appropriate culture containers, grown (expanded, multiplied) under appropriate culture conditions, harvested after an appropriate number of passages and subsequently lysed by mechanical, physical or chemical means. A typical procedure of the cell expansion process starting with one or more vials from the WCB (obtained as described in Example 2) is hereby given. A typical procedure of the fetal skin cell harvest and the subsequent cell lysis is given in Example 4.

On initiation day, one vial of the WCB (contained about 2 to 3 Mio cells; cells are at passage 3) was rapidly thawed in a 37°±2° C. water-bath until ice has just melted. The contents of the vial was added to about 9 ml of pre-warmed DMEM, 10% FCS and then centrifuged at approximately 200 g (about 936 rpm) for about 10 min in a Beckman GH3.8 swing out rotor (or equivalent). Post-centrifugation, the cell pellet is re-suspended in about 10 ml of fresh DMEM, 10% FCS and a sample was taken for cell counting. The cell suspension was then planted into four T225 Flasks (offering a cell culture surface of 225 cm$^2$, Nalge Nunc) in a total volume of about 40 ml DMEM, 10% FCS per flask and incubated in an incubator with 36.5°±1.5° C., 10±1% $CO_2$ and >80% humidity for 6 to 10 days until cultures approached confluence. Medium exchanges were performed every second or third day. Afterwards, the spent medium (conditioned culture medium) was aseptically removed from each flask and the cell sheets were washed with approximately 10 ml of pre-warmed PBS (37°±2° C.). After removal of PBS, approximately 3 ml of trypsin-EDTA (e.g. Invitrogen, Ref#25300-062) were added to each flask and allowed to cover the cell sheets in a horizontal position for approximately 1 min. The trypsin wash was then discarded to waste and an additional approximately 3 ml of trypsin-EDTA were added to each flask. The flasks were incubated at 36.5°±1.5° C. until the cells detached as observed visually or by microscope. The trypsin-EDTA was then neutralized by adding approximately 10 ml of DMEM, 10% FCS to each flask. The cell suspension was then centrifuged at approximately 200 g (about 936 rpm) for about 10 min in a Beckman GH3.8 swing out rotor (or equivalent). The resulting cell pellet was re-suspended in an appropriate volume of fresh DMEM, 10% FCS. A small sample (e.g. 0.5 ml) of cell suspension was removed for cell counting.

In the following, the so obtained cell suspension was expanded into 10 to 20 T500 Flasks (offering a cell culture surface of 500 cm$^2$, Nalge Nunc) at a seeding density of 2000 to 3000 cells per cm$^2$ in a total volume of 150 ml DMEM, 10% FCS per flask. The cell cultures were incubated in an incubator with 36.5°±1.5° C., 10±1% $CO_2$ and >80% humidity between 8 to 12 days until the cultures approached confluence. Medium exchanges were performed every second or third day. Afterwards, the spent medium (conditioned culture medium) was aseptically removed and the cell sheets were washed with approximately 30 ml of pre-warmed PBS (37° C.±2° C.). After removal of PBS, approximately 30 ml of trypsin-EDTA (e.g. Invitrogen, Ref#25300-062) were added to each flask and allowed to cover the cell sheets in a horizontal position for approximately 1 min. The trypsin wash was then discarded and about 30 ml of fresh trypsin-EDTA was added to each flask. The flasks were incubated at 36.5°±1.5° C. until the cells detached as observed visually or by microscope. The trypsin-EDTA was then neutralized by adding approximately 30 ml of DMEM, 10% FCS to each flask. The cell suspension was centrifuged at approximately 200 g (about 936 rpm) for about 10 min in a Beckman GH3.8 swing out rotor (or equivalent). The resulting cell pellet was re-suspended in an appropriate volume of fresh DMEM, 10% FCS. A small sample (e.g. 0.5 ml) of cell suspension was removed for cell counting.

The cell suspension was then expanded into 100 T500 Flasks at a seeding density of 2000 to 3000 cells per cm$^2$ in a total volume of about 150 ml DMEM, 10% FCS per flask. The cell cultures were incubated in an incubator with 36.5°±1.5° C., 10±1% $CO_2$ and >80% humidity for 8 to 12 days until the cultures approached confluence. Medium exchanges were performed every second or third day. This procedure allowed obtaining fetal skin cells at passage 6.

The person of skill in the art will understand that this cell expansion procedure can be extended to further passages similarly as described in this example with appropriate modifications to the given conditions. Generally, the cell expansion procedure is stopped between passages 6 to 10 and the cells are harvested as described in Example 4.

The person of skill in the art will understand that although the cell expansion is described using Culture Flasks, any number of roller bottles, multi-tray cell factories and/or cell bioreactors may be employed with appropriate modifications to the described conditions.

The skilled artisan will also understand that any number of methods of cell expansion can be employed. As a simple alternative to the described method, the cell expansion can be established in a 37° C., 5% $CO_2$ and >80% humidity incubator. Alternatively, the cell expansion can be established in serum free, partially serum free, and/or serum depleted culture media using conventional technology and cell culture methods.

Example 4

Fetal Skin Cell Harvest and Preparation of Fetal Skin Cell Proteins

A typical procedure of the fetal skin cell harvest and the subsequent fetal skin cell lysis in order to obtain fetal skin cell proteins is given in this example. The harvest of the fetal skin cells obtained after expanding (passaging, multiplying) one or more WCB vials as described in Example 3 is performed as follows:
1) Take flask (e.g.: T500 Flask) containing fetal skin cell culture and remove aseptically spent culture medium (conditioned culture medium).
2) Add appropriate volume of pre-warmed PBS (e.g.: approximately 30 ml for T500 Flask; at 37° C.±2° C.) to wash cell sheets. Rock flask gently back and forth to thoroughly wash cells and then remove aseptically PBS.
3) Add trypsin-EDTA (e.g.: approximately 50 ml for T500 Flask; e.g. Invitrogen Ref#25300-062) to flask to cover the cell sheets in a horizontal position for approximately 1 min
4) Discard trypsin-EDTA and then add fresh trypsin-EDTA (e.g.: approximately 50 ml for T500 Flask).
5) Place flask at 36.5°±1.5° C. until the cells detach as observed visually or by microscope
6) Add appropriate volume of culture medium DMEM, 10% FCS (e.g.: approximately 50 ml for T500 Flask) to neutralize trypsin-EDTA and pool cell suspension into sterile centrifugation tube.
7) Rinse flask with culture medium (e.g.: approximately 50 ml for T500 Flask) and transfer aseptically into the same centrifugation tube.
8) Centrifuge tube for appropriate time and speed at ambient temperature (e.g.: at approximately 200 g (about 936 rpm) for about 10 min in a Beckman GH3.8 swing out rotor (or equivalent))
9) Remove and discard supernatant.
10) Add appropriate volume of culture medium DMEM, 10% FCS to cell pellet (e.g.: approximately 50 ml for pellet obtained from one T500 Flask) and re-suspend cell pellet.
11) Remove sample to perform cell count
12) Centrifuge tube as before and discard supernatant culture medium
13) Add appropriate volume of phosphate buffered saline (PBS) to cell pellet (e.g. approximately 50 ml for pellet obtained from one T500 Flask) and re-suspend cell pellet to wash cells.
14) Centrifuge tube as before and discard supernatant culture medium
15) Repeat PBS washing steps 13 and 14
16) To cell pellet, add 1 ml PBS per 16'000'000 viable cells. Alternatively, 1 ml PBS can be added to a lower or higher fetal skin cell number in order to obtain a less or a more concentrated cell suspension, respectively. Preferred fetal skin cell suspensions are prepared by adding 1 ml PBS to 10,000,000 to 20,000,000 viable fetal skin cells.
17) Mix in order to completely re-suspend fetal skin cells in PBS.
18) Immediately after re-suspending the fetal skin cells (step 17), perform three cycles of freeze-thawing. One cycle consists of placing the tube (or cryovial) containing the fetal skin cell suspension into liquid nitrogen until the cell suspension is completely frozen and then placing the tube containing the frozen cell suspension into at water-bath of approximately 37° C. until the content completely thawed. As soon as the last residual ice dissolves when thawing, immediately re-freeze by placing the tube (or cryovial) containing the thawed cell suspension into liquid nitrogen until completely frozen. Alternatively, a mixture of dry ice in methanol (or other alcohols such as ethanol, iso-propanol, etc.) can be used for freezing. Thawing can be also performed at room temperature. This procedure allows cell lysis of fetal skin cells thereby obtaining fetal skin cell proteins.
19) Perform a standard cell viability assay (e.g. MTT-assay, ATP-assay, fluorescence-based assay, etc.) with a small sample of so obtained fetal skin cell proteins. The measured cell viability of fetal skin cell proteins should be below 10%. Preferentially, the fetal skin cell proteins should not contain any viable fetal skin cells and/or be of 0% cell viability. In case a cell viability of higher than 10% is measured, additional freeze-thaw cycles are performed (as described in step 18) with the suspension obtained after step 18) until a cell viability bellow 10% is reached. This procedure allows cell lysis of fetal skin cells thereby obtaining fetal skin cell proteins.
20) Optionally, the during steps 1 to 19 obtained fetal skin cell proteins can be treated, separated into supernatant and cell pellet, and/or purified in order to obtain fetal skin cell proteins of a desired composition, purity, strength and/or potency. For this purpose, the techniques as described in 'Protein Analysis and Purification—Benchtop Techniques' (Rosenberg I. M., Birkauser, Boston) are followed.
21) Eventually aliquot fetal skin cell proteins into appropriate cryovials (e.g. 3.6 ml internal thread cryovial from Nunc)
22) Store fetal skin cell proteins at minus 70° C. or lower until use.

The person of skill in the art will understand that although the cell harvest is described using Culture Flasks, any number of roller bottles, multi-tray cell factories and/or cell bioreactors may be employed with appropriate modifications to the described conditions.

The skilled artisan will also understand that, as an alternative to PBS, any other physiological buffer (e.g. PBS without $Ca^{++}$ and/or without $Mg^{++}$, HEPES, etc.) can be used to wash the fetal skin cells and to prepare the fetal skin cell suspension for cell lysis with appropriate modifications to the described conditions. The skilled artisan will also understand that, as an alternative to a physiological buffer, other aqueous systems (e.g. culture medias, non-physiological buffers, pH-buffer systems, water, etc.) can be used to prepare the fetal skin cell suspension for cell lysis. The skilled artisan will also understand that, the aqueous system used for freeze-thawing can be supplemented with cryoprotectants, protease inhibitors, glycosidase inhibitors, chemicals stabilizing proteins, chemicals preventing protein denaturation, antioxidants, preservatives, antimicrobial agents and/or other chemicals before cell lysis.

Furthermore, the skilled artisan will also understand that, as an alternative to freeze-thawing, a wide range of cell lysis techniques can be employed to disrupt the cells in order to obtain the fetal skin cell proteins with appropriate modifications to the described conditions.

The so obtained fetal skin cell proteins are also called 'Processed Skin Proteins', 'Processed Skin Cell Proteins', or PSP™.

Example 5

Characterization of Fetal Skin Cell Proteins

The fetal skin cell proteins were analyzed for the presence of cytokines using a commercial cytokine array (Cytokine Antibody Array C Series 1000.1, RayBiotech, Inc.). This array allowed simultaneously detecting multiple cytokine expression and is specifically designed for cell lysates. The analysis was performed according to the manufacturer's instructions of the array (RayBiotech, Inc) with the supernatant of the fetal skin cell proteins obtained after centrifugation. No further manipulation of the so-obtained supernatant was performed.

The fetal skin cell proteins were obtained as described in Examples 3 and 4 with fetal skin cells from a fetal skin cell bank (established as described in Example 2), which was initiated with a skin sample at about 16 weeks gestation (obtained as described in Example 1). Except the above described centrifugation of the fetal skin cell proteins, no purification, manipulations and/or supplementation (as described in Example 4) of the fetal skin cell proteins was performed.

The analysis revealed the presence of more than 100 cytokines in the fetal skin cell proteins. Proteins of most cytokine protein families including growth factors, interleukins, lymphokines, monokines, interferons, colony stimulating factors and chemokines were detected.

Cytokines detected include, but are not limited to epidermal growth factor (EGF), basic fibroblast growth factor (bFGF or FGF-2), beta nerve growth factor (b-NGF), fibroblast growth factors 4, 6 and 9 (FGF-4, FGF-6, FGF-9), granulocyte-colony stimulating factor (G-CSF), granulocyte-macrophage colony stimulating factor (GM-CSF), hepatocyte growth factor (HGF), insulin-like growth factor (IGF-I), interferon-gamma (IFN-γ), interleukins IL-1 alpha and IL-1 beta, interleukins IL-4, IL-6, IL-10 and IL-13, interleukin 1 receptor antagonist (IL-1ra), keratinocyte growth factor 1 (KGF-1 or FGF-7), placenta growth factor (PGF), platelet derived growth factor (PDGF), transforming growth factor beta 1 and 3 (TGF-β1, TGF-β3), tissue inhibitors of metalloproteinase 1 and 2 (TIMP-1, TIMP-2), vascular endothelial growth factor (VEGF). The presence of many other known cytokines (e.g.: TGF-β2, FGF-10, etc.) was not analyzed with this array.

Two-dimensional gel electrophoresis and mass spectrometry were further used to analyze the fetal skin cell proteins. The analyses were focused on a region of the gel corresponding to isoelectric point (pI) between 4 and 8 and molecular weight from 8000 to 35000. In this area 373±42 spots were detected (n=18). Some spots were analyzed and revealed the presence of several antioxidant enzymes including superoxide dismutase and thioredoxin peroxidase.

The person of skill in the art will understand that the fetal skin cell proteins (obtained as described above) contain many more cell derived proteins, extracellular matrix proteins, glycoproteins and/or other cellular constituents or bio-molecules such as lipids, fatty acids, fatty acid esters, monosaccharides, polysaccharides, DNA and RNA, inorganic material such as minerals and salts, etc.

Besides the analysis by cytokine array and two-dimensional gel electrophoresis described in this example, other appropriate analytical methods such as ELISA, GC, HPLC, HPLC coupled with mass spectroscopy and/or other analytical and/or proteomic platforms may be used to further characterize the fetal skin cell proteins.

Example 6

Activity of Fetal Skin Cell Proteins

The fetal skin cell proteins characterized in Example 5 were assessed for promoting human dermal fibroblast proliferation or cell growth. The fetal skin cell proteins were obtained as described in Examples 3 and 4 with fetal skin cells from a fetal skin cell bank (established as described in Example 2), which was initiated with a skin sample at about 16 weeks gestation (obtained as described in Example 1). No purification, manipulations and/or supplementation (as described in Example 4) of the fetal skin cell proteins was performed.

The proliferation assay was performed as follows. Normal human dermal fibroblast at passage 8 were seeded with DMEM (Invitrogen 21969035) and 10% FCS in 96-well plates at 5000 cells per well. The culture medium was changed by new DMEM with 2% FCS for 12 h. The culture medium was removed and changed by a new medium DMEM without FCS containing (or not; control) the tested compounds at differing concentrations. The cells were incubated for 48 h at 37° C. and 5% $CO_2$. The radiolabeled compound [$^3$H]-thymidine (Amersham TRK 686, 2.92 Tbq/mmole, 79 Ci/mmole) was added to each culture medium 24 h before the end of incubation. All treatments were performed in triplicate.

The analysis of incorporated radioactivity into DNA was performed after cell lysis and DNA collection by addition of 1 volume of chaotropic buffer (Tris/Hcl 50 mM, guanidine 4 M and EDTA 5 mM, pH 8.0), precipitation by trichloracetic acid (TCA), filter collection (collector and filters Skatron), wash cycles with TCA and 70% ethanol and subsequent quantification by liquid scintillation of the radioactivity specially incorporated into DNA (relative proliferative level).

The fetal skin cell proteins were tested at between 0.01% and 0.25% and resulted in a significant increase in thymidine incorporation at 0.05% and 0.25%. The increase was 305% and 361% of control, respectively. At 0.01%, a slight stimulation (127% of control) was observed.

Concluding, this in vitro test demonstrated that the fetal skin cell proteins enhance human dermal fibroblast proliferation about 3-fold or more at a concentration of 0.05% to 0.25%.

Example 7

Preparation of Compositions Comprising Fetal Skin Cell Proteins

This example illustrates the preparation of a series of compositions suitable for topical, mucosal, ocular, rectal and/or vaginal applications containing the fetal skin cell proteins. The fetal skin cell proteins were obtained as described in Examples 3 and 4 with fetal skin cells from a fetal skin cell bank (established as described in Example 2), which was initiated with a skin sample at about 16 weeks gestation (obtained as described in Example 1). No purification, manipulations and/or supplementation (as described in Example 4) of the fetal skin cell proteins was performed.

The fetal skin cell proteins are also called 'Processed Skin Proteins', 'Processed Skin Cell Proteins', or PSP™.

During in vitro experiments (as illustrated in Example 6) the optimal concentration of fetal skin cell proteins in the carrier suitable for topical, mucosal, ocular, rectal and/or vaginal applications was shown to be between 0.05% and 0.25%.

The following examples should illustrate the preparation of compositions containing either 0.050% or 0.065% fetal skin cell proteins.

An oil-in-water emulsion based cream containing 0.05% fetal skin cell proteins (obtained as described in Examples 3 and 4) was prepared using standard emulsifying techniques. The emulsion was obtained by combining an appropriate mixture of suitable ionic, zwitter-ionic and/or non-ionic surfactants with water (or mineral or spring water) and suitable oils. Suitable natural, refined and/or synthetic oils were used. Suitable natural oils include but are not limited to avocado oil, apricot oil, borage oil, borage seed oil, camellia oil, canola oil, castor oil, coconut oil, corn oil, cottonseed oil, evening primrose oil, palm oil, palm kernel oil, peanut oil, rapeseed oil, safflower oil, sweet almond oil, rose hip oil, *calendula* oil, chamomile oil, eucalyptus oil, juniper oil, safflower oil, sandalwood oil, tea tree oil, sunflower oil, soybean oil wheat germ oil and/or mixtures thereof. Generally, these oils are used refined and/or hydrogenated. Other suitable oils such as animal, mineral, silicon (or synthetic oils can be further used (e.g. lanolin, petrolatum, dimethicone, simethicone, caprylic/capric triglyceride, triclycerides, fatty acid esters, etc.). The formulation may further contain suitable emollients and/or humectants such as glycerin, propylene glycol, butylene glycol, 1,3-butylene glycol, hexylene glycol, decyl oleate, cetearyl alcohol, cetyl palmitate, glyceryl stearate and/or mixtures thereof. The emulsion may also contain one or a combination of suitable antioxidants such as tocopherol, tocopheryl acetate, ascorbic acid, ascorbyl palmitate, magnesium ascorbate, beta-carotene, BHT, ferulic acid, lipoic acid, coenyzme Q10, flavonoids, green tea extracts, white tea extracts, poly-phenolic compounds, uric acid, selenium and/or any derivatives thereof. Selected salts such as sodium chloride, potassium chloride, magnesium chloride and phosphate salts may be further added. Sugars, such as sucrose, glucose, maltose dextrose and fructose, hydric alcohols, such as sorbitol, mannitol, xylitol and maltitol, and polymers such as carbomers, polydextrose, xanthan gum, guar gum, sodium alginate, carrageenan, hydroxypropyl cellulose (HPC), hydroxypropyl methylcellulose (HPMC), methylcellulose, polyvinylpyrrolidone (PVP), maltodextrin, carbomers, polyvinyl alcohol, polyethylene glycol (PEG), polyethylene oxide, carboxymethylcellulose (CMC) and hydroxyethyl cellulose (HEC) are examples of suitable rheology modifiers to increase viscosity of the preparation.

The fetal skin cell proteins were mixed into the outer, aqueous phase of the oil-in-water emulsion cream as one of the final steps during the preparation of the oil-in-water emulsion based compositions. The mixing of the fetal skin cell proteins into the formulation was realized at ambient or only slightly elevated temperature.

Cream 1, 2 and 3 (ingredients are given below) were obtained after preparing the cream base (formulation without fetal skin cell proteins) using standard emulsifying techniques and then, once the cream base reached room temperature (between 20° to 30° C.), mixing the fetal skin cell proteins into the cream base using appropriate, standard mixing methods and equipments.

Mixing methods and equipments comprise methods to mix, blend, emulsify, homogenize and/or disperse the cream base with the fetal skin cell proteins as described above.

Thereby, the fetal skin cell proteins were diluted with an appropriate volume of water before mixing the resulting suspension (dispersion) into the cream base. Generally, the fetal skin cell proteins were diluted with water to give of 2 to 5% in volume (or weight) of the final composition (formulation). In one of the preferred embodiment, the fetal skin cell proteins were added to water to give 3% in volume of the final formulation, which was then added and mixed with 97% of the previously prepared cream base using appropriate, standard mixing methods and equipments.

Alternatively, preservatives (e.g.: parabens, phenoxyethanol, imidazolidinyl urea, isothiazolinones, glycols, etc.), protein stabilizing agents (e.g.: amino acids, polyols, sugars, synthetic polymers, PEGs, PEG-PPG-PEGs, hyaluronic acid, sodium hyaluronate, fibronectin, actin, collagen, EDTA, etc.), protease inhibitors and/or antioxidants can be added in appropriate concentrations to the so-prepared fetal skin cell protein suspension before addition to the cream base.

The person of skill in the art will understand that there are differing methods to prepare oil-in-water emulsion based creams. Alternatively, fetal skin cell proteins can be also mixed into water-in-oil emulsion based creams with appropriate modifications to the described conditions.

Cream 1:

An oil-in-water cream containing 0.05% fetal skin cell proteins (or PSP) was prepared as described above and contained the following other ingredients in order of descending predominance: water, hydrogenated peanut oil, glycerin, cetearyl ethylhexanoate, cetearyl alcohol, PEG-8 C12-18 alkyl ester, PPG-25-laureth-25, PEG-5 pentaerythrityl ether, hydroxyethylcellulose, cetyl alcohol, cetyl palmitate, glyceryl stearate, sodium chloride, ascorbyl palmitate, glucose, simethicone, tocopheryl acetate, citric acid, ricinoleth-40, potassium chloride and magnesium chloride. The cream further contained a mixture of methylparaben, propylparaben and imidazolidinyl urea for antimicrobial preservation.

Cream 2:

An oil-in-water cream containing 0.05% fetal skin cell proteins (or PSP) was prepared as described above and contained the following other ingredients in the following order of descending predominance: water, octyldodecanol, glyceryl stearate decyl oleate, glycerin, propylene glycol, *triticum vulgare* (wheat germ oil), stearic acid, cetyl alcohol, ceteareth 20, myreth-3 myristate, ceteareth 12, cetearyl alcohol, cetyl palmitate, tocopheryl acetate, dimethicone, borago officinalis (borage seed oil), carbomer, triethanolamine, methylparaben, propylparaben, glycophingolipids, disodium EDTA and BHT. The cream further contained a mixture of phenoxyethanol, ethylparaben, butylparaben, methylisothiazolinone and methylchloroisothiazolinone for antimicrobial preservation.

Cream 3:

An oil-in-water cream containing 0.065% fetal skin cell proteins (or PSP) was prepared as described above and contained the following other ingredients in the following order of descending predominance: water, caprylic/capric triglyceride, C12-20 acid PEG-8 ester, butylene glycol, glycerin, saccharide isomerate, PEG-8, cetyl alcohol, caprylyl glycol, potassium cetyl phosphate, carbomer, bisabolol, ascorbyl tetraisopalmitate, caffeine, disodium EDTA, phospholipids, glycyrrhetinic acid, sodium hyaluronate, sodium polyacrylate, citric acid, propylparaben, tocopherol, beech tree bud extract (*fagus sylvatica* extract), palm oil (*elaeis guineensis*), tocotrienols, ascorbyl palmitate, squalene, ascorbic acid and phytosterols. The cream further contained a mixture of phenoxyethanol, methylparaben, butylparaben, ethylparaben and isobutylparaben for antimicrobial preservation.

Cream 4:

An oil-in-water cream containing 0.05% fetal skin cell proteins (or PSP) was prepared as described above and contained the following other ingredients in order of descending predominance: water, caprylic/capric triglyceride, C12-20 acid PEG-8 ester, coco-caprylate/caprate, butylene glycol, dimethicone, phenyl trimethicone, biosaccharide gum-1, glycerin, cetyl alcohol, phenoxyethanol, saccharide isomerate, carbomer, potassium cetyl phosphate, borago officinalis (borage seed oil), ascorbyl tetraisopalmitate, caprylyl glycol, methylparaben, disodium EDTA, *chondrus crispus* (carrageenan), sodium hyaluronate, *elaeis guineensis* (palm) oil, tocotrienols, phytosterols, butylparaben, ethylparaben, PEG-8, isobutylparaben, propylparaben, tocopherol, citric acid, ascorbyl palmitate, squalene and ascorbic acid.

Cream 5:

An oil-in-water cream containing 0.05% fetal skin cell proteins (or PSP) was prepared as described above and contained the following other ingredients in order of descending predominance: water, ethylhexyl methoxycinnamate, C12-20 acid PEG-8 ester, caprylic/capric triglyceride, coco-caprylate/caprate, butylene glycol, butyl methoxydibenzoylmethane, cetyl alcohol, biosaccharide gum-1, glycerin, C12-15 alkyl benzoate, saccharide isomerate, phenoxyethanol, caprylyl glycol, titanium dioxide, potassium cetyl phosphate, carbomer, borago officinalis seed oil, ascorbyl tetraisopalmitate, methylparaben, sodium hydroxide, disodium EDTA, *chondrus crispus* (carrageenan), sodium hyaluronate, *elaeis guineensis* (palm) oil, tocotrienols, phytosterols, butylparaben, aluminium stearate, polyhydroxystearic acid, ethylparaben, alumina, PEG-8, isobutylparaben, propylparaben, tocopherol, citric acid, BHT, ascorbyl palmitate, squalene and ascorbic acid.

Creams 1 to 5 contain selected antioxidants such as ascorbic acid, BHT, tocopherol and tocotrienols as well as some derivatives thereof (ascorbyl palmitate, ascorbyl tetraisopalmitate, tocopheryl acetate).

Creams 3 to 5 contain protein stabilizing agents such as sodium hyaluronate, biosaccharide gum-1 and/or saccharide isomerate.

Creams 2 to 3 contain a protease inhibitor: EDTA or disodium EDTA.

Cream 5 contains sunscreens (ethylhexyl methoxycinnamate, titanium dioxide).

Hydrogels are hydrophilic, three-dimensional networks, which are able to imbibe large amounts of water or biological fluids, and thus resemble, to a large extent, a biological tissue (Peppas N. A. et al. Eur J Pharm Biopharm. 2000, 50:27-46). They are insoluble due to the presence of chemical (tiepoints, junctions) and/or physical cross-links such as entanglements and crystallites. These materials can be synthesized to respond to a number of physiological stimuli present in the body, such as pH, ionic strength and temperature.

Hydrogels are based on hydrophilic polymers, which are cross-linked to prevent dissolution in water. Because hydrogels can contain large amounts of water, they are interesting devices for the delivery of proteins (Int J Pharm. 2004; 277: 99-104.).

Alginates, collagens, dextrans, gelatins, starch, dextranlactates, hyaluronic acid, chitosans, poly(vinyl alcohol) (PVA), ethylene vinyl acetate poly-1-lactide, ceramic hydroxyapatite, N-vinylpyrrolidone, polyethylene glycol, poly(ethylene)-b-poly(propylene oxide) co-polymers (Pluronics®) and derivatives thereof can be used to obtain hydrogels when mixed with water or an aqueous solution.

The hydrogels are obtained after chemical or physical crosslinking linking. Cross-linking can be obtained via glutaraldehyde treatment, aggregation during freeze-thaw treatment, and radiation-induced crosslinking (e.g. UV light) or chain scission of loaded proteins. Stereocomplex formation between enantiomeric oligomeric lactic acid chains after mixing aqueous solutions of dextran(l)-lactate and dextran (d)-lactate is a method of physical crosslinking (Int J Pharm. 2004; 277: 99-104.).

Gel 1:

A gel containing 0.05% fetal skin cell proteins (or PSP) was prepared using Poloxamer 407 (Lutrol F127, BASF) between 15 to 22%. Preservatives were also added.

Example 8

Treatment of Vulvodynia and/or Vulvar Vestibulitis with Composition

Cream 1 (prepared as described in Example 7) and Cream 2 (prepared as described in Example 7); two similar oil-in-water emulsion based formulations and both containing 0.05% fetal skin cell proteins, were evaluated under in use conditions for treating vulvar vestibulitis syndrome.

During the first 6 to 8 weeks, the vulvar vestibulitis patients applied the cream twice daily (morning and evening) around the lower part of the vestibule in a U-shape manner from 3 o'clock to 9 o'clock by using their index finger. Per application, about 0.2 ml (corresponding to about the size of a green pea) of cream were applied. After 6 to 8 weeks, they continued the application once a day until the symptoms stabilized or disappeared. Once the symptoms stabilized or disappeared, they continued with the application of the cream once a day or at their convenience in order to avoid reoccurrence of the symptoms.

Cream 1 was tested in a panel of 13 women (between 20 to 39 years of age; 28±5 years) with long-term history of vulvar vestibulitis (between 2 to 10 years; 4±3 years). The cream's efficacy was evaluated subjectively during a patient interview inquiring quality of their sex life as endpoint. All patients reported an improved quality of sex life after 3 to 8 weeks (5±2 weeks) of twice daily cream use (FIG. 1). 62% of the patients reported to be able to have normal, pain free intercourse after this period. 31% reported a much better and one patient (8%) a better sex life. The cream was well tolerated in all patients; no signs for irritation, allergy, tachyphylaxis or change in vaginal flora were reported or observed.

Cream 2 was tested in a panel of 10 women (between 17 to 30 years of age; 23±4 years) with long-term history of vulvar vestibulitis (between 1 to 3 years; 2±1 years). The cream's efficacy was evaluated subjectively during a patient interview inquiring quality of their sex life as endpoint.

Figure 2:
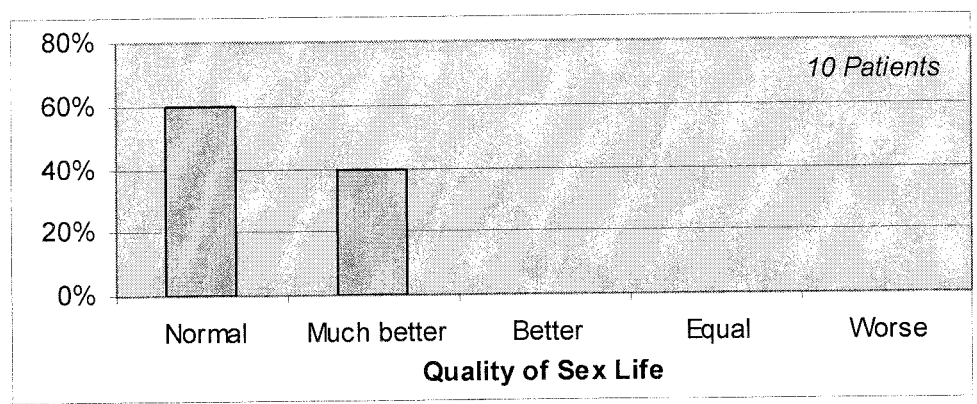
FIG. 2 is a graph showing the efficacy of Cream 2 containing 0.05% fetal skin cell proteins in treating vulvar vestibulitis syndrome as assessed by a quality of sex life interview.
Figure 3:
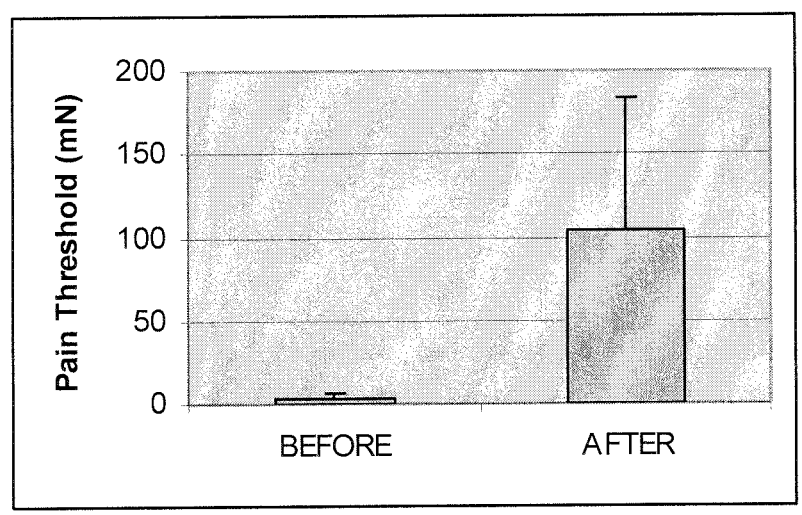
FIG. 3 is a graph showing the efficacy of Cream 2 containing 0.05% fetal skin cell proteins in treating vulvar vestibulitis syndrome as assessed by measuring vulvar pain threshold before and after treatment. Pain threshold is given in milli Newton (mN); mean and standard deviation are given (n=6).

All patients reported an improved quality of sex life after 2 to 8 weeks (5±2 weeks) of twice daily cream use (FIG. 2). 60% of the patients reported to be able to have normal, pain free intercourse and 40% reported a much better sex life after this period. The cream was well tolerated in all patients; no signs for irritation, allergy, tachyphylaxis or change in vaginal flora were reported or observed.

In addition to the subjective assessment of vulvar pain by interview, vulvar pain thresholds were determined quantitatively before and after treatment with the Semmes Weinstein Von Frey Aesthesiometer (also called Frey Filaments) in six of these women. The women were between 17 to 30 years (24±5 years) of age with a history of vulvar vestibulitis for 1 to 2 years (2±0 years).

A significant, 30-fold increase in the averaged vulvar pain threshold from 3.7±3.2 mN to 112.6±80.7 mN was measured after 8 weeks of twice daily use of Cream 2, what confirmed the results obtained by interview. This latter value is close to the 158±33 mN reported by Bohm-Starke et al. (Pain 2001, 94, 177-183) for healthy women.

Combined, these results demonstrate that the improved sex life reported by the patients after and/or during treatment with the cream is the result of the ability to have intercourse and/or other sexual activities with reduced or no pain. In addition to an increased pain threshold upon pressure induced to vaginal penetration or friction and rubbing of the vagina and vulvar region, the repeated use of Cream 1 and 2 as described above further resulted in decrease of vestibular redness or erythema (in case present before use of the creams), pruritus (itch) and burning sensations.

Concluding, the cream demonstrated to be beneficial in treating vulvar vestibulitis syndrome.

Example 9

Treatment of Vulvar Lichen Sclerosus with Composition

Cream 2 (prepared as described in Example 7) was tested in a panel of 9 women (between 17 to 30 years of age; 23±4 years) with vulvar lichen sclerosus. The cream's efficacy was evaluated visually by a gynecologist. Twice daily application of Cram 2 on the vulva resulted in a significant improvement of vulvar lichen sclerosus symptoms. The cream was well-tolerated without occurrence of local or systemic adverse effects.

Concluding, the cream demonstrated to be beneficial in treating vulvar lichen sclerosus.

Example 10

Treatment of Atopic Dermatitis or Eczema with Composition

Cream 1 (prepared as described in Example 7), an oil-in-water emulsion based formulations containing 0.05% fetal skin cell proteins, was evaluated under in use conditions for atopic dermatitis or eczema during two studies.

In one study, Cream 1 was studied on 5 patients with atopic and/or irritative hand eczema. The patients were between 17 and 58 years old (33±16 years). At the beginning of the treatment, the patients applied the cream twice to three times daily. Later, the frequency of applications was reduced to once to twice daily. The patients applied the cream between one to several months. Global assessment, and symptoms such as pruritus, erythema, vesicles, edema, scaling, lichenification and cracks or crevices were assessed using a 0 to 4 scale (0=no symptoms, 1=mild, 2=moderate, 3=severe, 4=very severe) before and after treatment.

Figure 4:
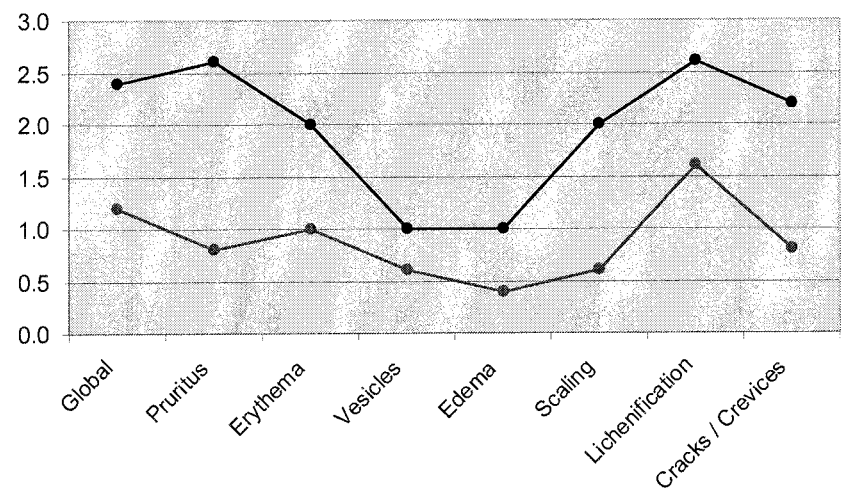
FIG. 4 is a graph showing the efficacy of Cream 1 containing 0.05% fetal skin cell proteins in treating hand eczema. The following scoring system: 0=not present, 1=slight, 2=moderate, 3=severe, and 4=very severe was used to assess the symptoms before (black curve) an after (red) treatment. Mean values are given; n=5.

In all but one patient, the overall severity of eczema (global assessment) decreased by at least 1-point after one to six months of cream use (FIG. 4). Particularly worth mentioning are the significantly reduced pruritus (itch) symptoms and the largely reduced presence of scales, cracks or crevices after cream use. Pruritus was completely reduced in all but one patient; the individual itch or pruritus scores were reduced 80% in average. In addition, individual scores for erythema was reduced 58%, for vesicles 50%, for edema 67%, for fissures 53%, for lichen 28% and for crevices 53% in average for all five subjects.

The cream was well-tolerated without occurrence of local or systemic adverse effects.

In another study, Cream 1 was studied on 23 patients with eczema, whereas 15 suffered from severely creviced and chapped hands; a form of hand eczema. The patients were between 5 and 75 years of age. The patients applied the cream up to three times daily during the evaluation period.

Appearance and symptoms of hand eczema improved significantly in all but one patient after some weeks to a few months of continued use. The cream was well-tolerated without occurrence of local or systemic adverse effects.

Concluding, Cream 1 demonstrated to be beneficial in treating eczema; particularly for hand eczema, and cures creviced and chapped hands.

Example 11

Treatment of psoriasis with composition

Cream 1 (prepared as described in Example 7) was tested in a panel of 3 patients with psoriasis. The patients applied the cream up to three times daily during the evaluation period. Appearance and symptoms of psoriasis improved significantly (FIG. 5) in all but one patient. This patient did not apply the cream as described in the study protocol. Treatment was effective after some weeks to few months of daily application. The cream was well-tolerated without occurrence of local or systemic adverse effects.

Concluding, Cream 1 demonstrated to be beneficial in treating psoriasis.

Example 12

Treatment of rosacea with composition

Cream 2 (prepared as described in Example 7) was tested in a several rosacea patients in combination with skin care regimens and/or rosacea medication. Two representative rosacea cases are reported below; one without (Case 1) and one with concomitant seborrheic dermatitis (Case 2).

Figure 6:
FIG. 6 is a photograph showing the efficacy of Cream 2 containing 0.05% fetal skin cell proteins in treating rosacea in combination with an alpha hydroxy acid (glycolic acid) product. A representative example of a rosacea patient is shown before and after cream use for two weeks.
Figure 6:
Figure 6:
Figure 6:

In one study, prior to use of Cream 2 (prepared as described in Example 7), the rosacea patient (Caucasian women, 58 years), used MD Forte Facial Cleanser II (contains 15% glycolic compounds), MD Forte Replenish Hydrating Cream and Physiogel® Cream (Stiefel Laboratories) for 6 weeks twice daily without marked improvements of erythemato telangiectatic rosacea (FIG. 6, photo Before).

Administration of Physiogel® Cream was stopped and the patient used Cream 2 instead, together with the same facial cleanser and hydrating cream as used during the first 6 weeks. A marked decrease in the erythema of rosacea of the entire face, forehead, nose, cheeks and chin was observed after two weeks twice daily application of Cream 2 (FIG. 6, photo After).

In another study, prior to use of Cream 2 the patient (Caucasian women, 41 years) with six month history of rash on forehead (scalp clear) was treated with Elocon® (0.1% mometasone furoate ointment; Schering Cop.) for two weeks. Use of Elocon® was stopped and after one week the forehead flared again.

Figure 7:
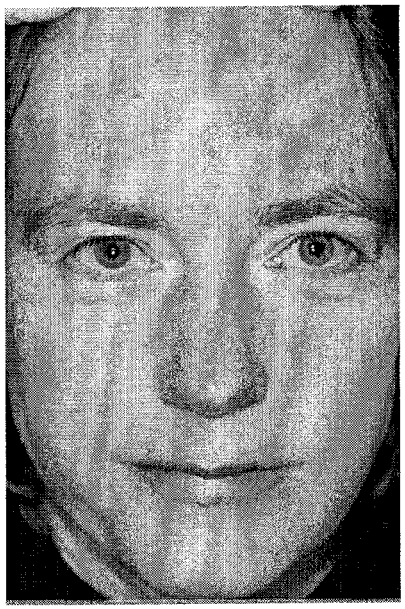
FIG. 7 is a photograph showing the efficacy of Cream 2 containing 0.05% fetal skin cell proteins in treating rosacea with concomitant seborrheic dermatitis in combination with rosacea medication (azelaic acid product). A representative example of a rosacea patient with concomitant seborrheic dermatitis is shown before and after cream use for seven weeks.
Figure 7:
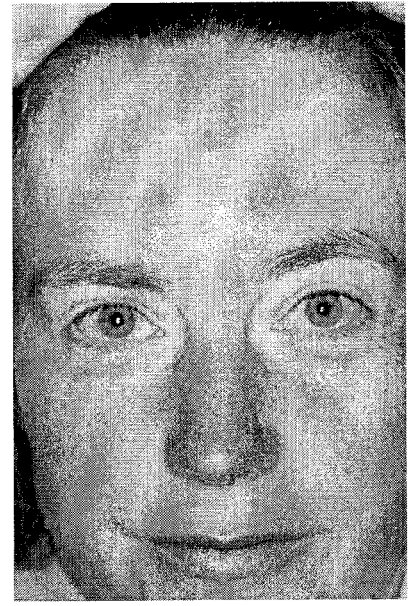
Figure 7:
Figure 7:

The patient applied then Finacea® Gel (distributed by Berlex Laboratories) twice daily for 4 weeks in combination with a RH cleanser and RH cream. The seborrheic dermatitis and rosacea improved at least 75% during this period with a decrease in all inflammatory lesions and erythema across the forehead (FIG. 7, Before photo).

After this period, the patient started to use Cream 2 in combination with Finacea® Gel (gel was applied first) together with the RH cleanser and the RH cream. The addition of Cream 2 to the treatment regimen helped the patient to quasi recover from the symptoms. After 7 weeks twice daily application, a marked, further improvement of the seborrheic dermatitis and rosacea was observed (FIG. 7, After photo).

Rosacea patients tolerated the cream well-without occurrence of local or systemic adverse effects.

Concluding, Cream 2 demonstrated to be beneficial in treating psoriasis.

Example 13

Treatment of Minor Wounds and/or Burns with Composition

Cream 1 (prepared as described in Example 7) and Cream 2 (prepared as described in Example 7); two similar oil-in-water emulsion based formulations and both containing 0.05% fetal skin cell proteins, were evaluated under in use conditions for treating minor wounds and/or burns.

Cream 1 was tested in a panel of 8 patients with $1^{st}$ degree burns. The patients were between 5 and 68 years of age. The patients applied the cream up to three times daily during the evaluation period. Appearance and symptoms of burns improved significantly in all patients. Treatment was effective after some weeks of daily application. The cream was well-tolerated without occurrence of local or systemic adverse effects.

Figure 8:
FIG. 8 is a photograph showing the efficacy of Cream 2 as treatment after minor wounds and/or skin lesions obtained after cryosurgery. Cryosurgery (or cryotherapy) was performed to remove age spots on hands. The pictures after cryosurgery (photo Before; corresponding to before cream use) and after 6 weeks twice daily cream use are shown (After).
Figure 8:
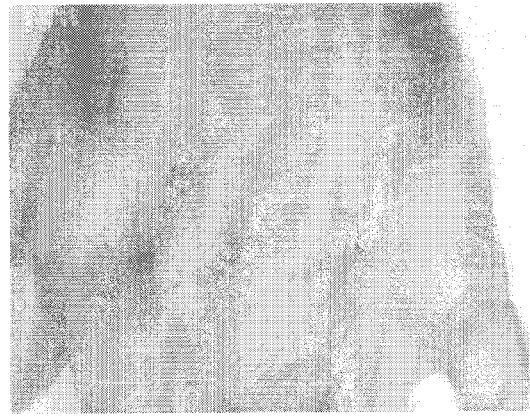

Cream 2 was tested for the treatment of skin lesions obtained after cryosurgery to remove age spots on hands. 6 weeks of twice daily cream application lead to a rapid healing of the skin lesions and resulted in a significantly improved appearance, tone and texture of skin (FIG. 8)

Concluding, Cream 1 and Cream 2 demonstrated to be beneficial in treating minor wounds such as $1^{st}$ degree burns and skin lesions after cryosurgery.

Example 14

Treatment of Scars and Keloids

Cream 1 (prepared as described in Example 7) was tested in a panel of 11 patients with scars and recent keloid formation. The patients were between 53 and 68 years of age. The patients applied the cream up to three times daily during the evaluation period. Appearance of scars and keloids improved significantly in all patients where the scar was present for not more than one year. Treatment was effective after some weeks to few months of daily application. The cream was well-tolerated without occurrence of local or systemic adverse effects.

Concluding, Cream 1 demonstrated to be beneficial in freshly formed scars and keloids (less than one year).

Example 15

Use of Composition as Treatment after Skin Auto-, or Allografting

Cream 1 (prepared as described in Example 7), an oil-in-water emulsion based formulations containing 0.05% fetal skin cell proteins, was evaluated under in use conditions for wound care after skin grafting of burns and ulcers.

Cream 1 was tested in a panel of 8 children suffering from a $2^{nd}$ and $3^{rd}$ degree burns. As a standard procedure, the cream was applied after complete or partial wound closure due to the application of one or more skin cell constructs. In addition, the cream was also applied at skin sites adjacent to the graft where the skin was burned to a minor degree. The patients were between 14 months to and 9 years of age. Body sites included hand, arm, foot, leg and buttocks. The cream was applied up to three times daily during the evaluation period. Appearance, texture and tone of skin at the wounded site and scar-formation improved significantly in all patients. Treatment with the cream was effective after some weeks to few months of daily application. The cream was well-tolerated without occurrence of local or systemic adverse effects.

Concluding, Cream 1 demonstrated to be beneficial in the post-treatment of burns after skin auto-, or allografting. In addition, the cream can be successfully used in combination with the skin grafts in order to complete wound healing. The cream was safe when applied on children. Further, the cream was well-tolerated when applied on skin with compromised skin barrier properties.

Cream 1 was tested in a panel of 13 patients suffering from a pressure or diabetic ulcer. As a standard procedure, the cream was applied after complete or partial wound closure due to the application of one or more skin cell constructs. In addition, the cream was also applied at skin sites adjacent to the graft and peri-ulcerous skin. And, once the wound closed or became too small for a subsequent construct application, the cream was applied twice daily as follow-up treatment. The patients were between 10 days to and 85 years of age. Body sites included calf, ankle, foot and arm. The cream was applied up to three times daily during the evaluation period.

Appearance, texture and tone of skin at the ulcered site and scar-formation improved significantly in all but one patient. Treatment in this patient was stopped due to diagnosed diabetics. In one male patient (85 years of age), the disease recurred after initial successful treatment. As an example, a child born with a pressure ulcer to the muscle layer on the arm was successfully treated at 10 days of age. The baby received three skin grafts and was treated in parallel with the cream. After wound closure on day 15 of treatment, cream was applied on the entire skin area for several weeks resulting in a perfect and scar-less wound healing. In most cases, treatment with the cream was effective after some weeks to few months of daily application. The cream was well-tolerated without occurrence of local or systemic adverse effects.

Concluding, Cream 1 demonstrated to be beneficial in the post-treatment of ulcers after skin auto, or allografting. In addition, the cream can be successfully used in combination with the skin grafts in order to complete wound healing. The cream was safe when applied on newborn children. Further, the cream was well-tolerated when applied on skin with compromised skin barrier properties.

Example 16

Use of Composition as Treatment of Atrophie Blanche

Atrophie blanche is a particular type of scar arising on the lower leg. It occurs after a skin injury when the blood supply is poor. It is the characteristic lesion of livedoid vasculitis. Livedoid vasculitis is a rare, chronic vascular disorder characterized by persistent painful ulceration of the lower extremities. Livedoid vasculitis characteristics include (1) painful red or purple marks and spots that progress to small, tender, irregular ulcers (30% of cases), and (2) painless atrophie blanche scars.

Cream 1 (prepared as described in Example 7) was tested in a panel of 3 patients with atrophie blanche. The patients were between 37 and 76 years of age. The patients applied the cream up to three times daily during the evaluation period. Appearance and symptoms of atrophie blanche significantly decreased in all patients with significant stabilization of atrophic skin and surrounding area. Treatment was effective after some weeks to few months of daily application. The cream was well-tolerated without occurrence of local or systemic adverse effects.

Concluding, Cream 1 demonstrated to be beneficial in treating atrophie blanche.

Example 17

Use of Composition as Treatment for Other Skin Conditions, Disorders and Diseases Diverse in use studies demonstrated significant efficacy of Cream 1 and/or Cream 2 (prepared as described in Example 7; both oil-in-water emulsion based formulations containing 0.05% fetal skin cell proteins) in treating, relieving or improving appearance of radiodermatitis, contact urticaria, contact dermatitis or irritant contact dermatitis, allergic contact dermatitis, sunburn and/or photo-dermatitis, generalized itch or pruritus, external rectal itch or pruritus, localized itch or pruritus on penis or scrotum, localized itch or pruritus due to poison oak and poison ivy exposure as well as insect bites and/or localized itch or pruritus on scar or keloid skin sites.

Example 18

Use of Composition as Treatment after Cosmetic/Dermatological Procedures

Diverse in use studies demonstrated significant efficacy of Cream 2 (prepared as described in Example 7) to improve recovery, skin regeneration and/or healing after chemical peels, dermabrasions and microdermabrasions, light and laser treatments, radiofrequency treatments, thermal treatments, electrosurgical resurfacing or coblation ($CO_2$-laser and radiofrequency), superfluous hair removal, diverse cosmetic surgery procedures, cryosurgery and/or diverse other cosmetic and dermatological procedures.

The treatment with the cream helps to enhance skin healing and recovery after those treatments resulting in an improved appearance, tone and texture of skin.

Example 19

Use of Composition for Reducing Signs of Skin-Aging

Figure 9:
FIG. 9 is a photograph showing the efficacy of Cream 2 in improving appearance of skin's fine lines and wrinkles including the nasal-labial fold in 54 year old women: before (left picture) and after 6 weeks of twice daily application (right).
Figure 9:

An in use study demonstrated significant efficacy of Cream 2 (prepared as described in Example 7) in improving appearance, tone and texture of facial fine lines and wrinkles including the nasal-labial fold (FIG. 9).

We claim:

1. A topical composition for treating a subject suffering from a skin condition, disorder or disease consisting essentially of an effective amount of lysate of cultured human fetal skin cells comprising human fetal skin proteins, wherein said cells were obtained from a cell bank prepared in vitro by cultivation and expansion of undifferentiated human fetal skin cells obtained from a human donor tissue of 12-16 weeks gestation, and a pharmaceutically or cosmetically acceptable topical carrier, wherein said lysate is incorporated in said composition at a concentration of between about 0.01% to about 5% by weight or volume of the final composition that is capable of promoting human dermal fibroblast proliferation, wherein said topical composition is capable of scarless wound healing upon topical administration, and wherein said topical composition is formulated in the form of an oil-in-water or water-in-oil emulsion or emulsion based cream, gel or hydrogel.

2. The composition of claim 1, wherein said undifferentiated fetal skin cells are obtained from whole fetal skin tissue.

3. The composition of claim 1, wherein said undifferentiated fetal skin cells are obtained from fetal skin tissue fragments.

4. The composition of claim 1, further comprising analgesics, anesthetics, anti-inflammatory agents, antihistamine agents, antioxidants, counter irritants, antimicrobial agents, antibacterial agents, antifungal agents, preservatives, protein stabilizing agents, protease inhibitors, skin protectant agents, sunscreens or combinations and mixtures thereof.

5. The composition of claim 1, wherein said composition is suitable for mucosal, ocular, rectal or vaginal administration.

6. The composition of claim 1, wherein said lysate is incorporated in said composition at a concentration of 0.05% by weight or volume of the final composition.

7. The composition of claim 1, wherein said lysate is incorporated in said composition at a concentration of 0.065% by weight or volume of the final composition.

8. The composition of claim 1, wherein said lysate incorporated in said composition at a concentration of between 0.05% to 0.25% by weight or volume of the final composition.

9. The composition of claim 1, wherein said cell lysate is obtained by induced cell lysis.

10. The composition of claim 9, wherein said cell lysis is performed by one or more cycles of freeze-thawing.

11. The composition of claim 9, wherein said cell lysis is performed with between 100 to 60/000,000 of cultured human fetal skin cells suspended in one milliliter of an aqueous system.

12. The composition of claim 11, wherein said cell lysis is performed with between 10,000,000 to 20,000,000 of cultured human fetal skin cells suspended in one milliliter of an aqueous system.

13. The composition of claim 11, wherein said aqueous system is a physiological buffer system.

14. The composition of claim 11, wherein said aqueous system is a phosphate buffered saline system.

15. The composition of claim 1, wherein said fetal skin proteins comprise one or more cytokines selected from the group consisting of epidermal growth factor (EGF), basic fibroblast growth factor (bFGF or FGF-2), beta nerve growth factor (b-NGF), fibroblast growth factors 4, 6 and 9 (FGF-4, FGF-6, FGF-9), granulocyte-colony stimulating factor (G-CSF), granulocyte-macrophage colony stimulating factor (GM-CSF), hepatocyte growth factor (HGF), insulin-like growth factor (IGF-I), interferon-gamma (IFN-γ), interleukins IL-1 alpha and IL-1 beta, interleukins IL-4, IL-6, IL-10 and IL-13, interleukin 1 receptor antagonist (IL-1ra), keratinocyte growth factor 1 (KGF-1 or FGF-7), placenta growth factor (PGF), platelet derived growth factor (PDGF), transforming growth factor beta 1 and 3 (TGF-β1, TGF-β3), tissue inhibitors of metallo-proteinase 1 and 2 (TIMP-1, TIMP-2), and vascular endothelial growth factor (VEGF).

16. The composition of claim 1, wherein said dermal fibroblast proliferation is enhanced about 3-fold.

\* \* \* \* \*